United States Patent
Tinger et al.

(10) Patent No.: US 12,037,314 B2
(45) Date of Patent: Jul. 16, 2024

(54) PROCESSES FOR ISOMERIZING C8 AROMATIC HYDROCARBONS

(71) Applicant: ExxonMobil Chemical Patents Inc., Baytown, TX (US)

(72) Inventors: Robert G. Tinger, Friendswood, TX (US); Hari Nair, Spring, TX (US); Todd E. Detjen, Bellaire, TX (US); Paul Podsiadlo, Humble, TX (US); Travis D. Sparks, Deer Park, TX (US)

(73) Assignee: ExxonMobil Engineering & Technology Company, Baytown, TX (US)

( * ) Notice: Subject to any disclaimer, the term of this patent is extended or adjusted under 35 U.S.C. 154(b) by 39 days.

(21) Appl. No.: 17/631,679

(22) PCT Filed: Aug. 11, 2020

(86) PCT No.: PCT/US2020/045725
§ 371 (c)(1),
(2) Date: Jan. 31, 2022

(87) PCT Pub. No.: WO2021/041021
PCT Pub. Date: Mar. 4, 2021

(65) Prior Publication Data
US 2022/0274900 A1    Sep. 1, 2022

Related U.S. Application Data

(60) Provisional application No. 62/890,935, filed on Aug. 23, 2019.

(30) Foreign Application Priority Data

Nov. 14, 2019   (EP) ..................................... 19209114

(51) Int. Cl.
*C07C 5/27*       (2006.01)
*B01J 29/42*      (2006.01)

(52) U.S. Cl.
CPC ............. *C07C 5/2708* (2013.01); *B01J 29/42* (2013.01)

(58) Field of Classification Search
CPC ......... C07C 5/2708; C07C 15/08; B01J 29/42
See application file for complete search history.

(56) References Cited

U.S. PATENT DOCUMENTS

| | | |
|---|---|---|
| 3,040,777 A | 6/1962 | Carson et al. |
| 3,201,491 A | 8/1965 | Stine et al. |
| 3,422,848 A | 1/1969 | Liebman et al. |
| 3,651,162 A | 3/1972 | Pohlmann et al. |
| 3,662,013 A | 5/1972 | Machell et al. |
| 3,761,533 A | 9/1973 | Mori et al. |
| 3,856,872 A | 12/1974 | Morrison |
| 3,919,339 A | 11/1975 | Ransley |
| 4,029,717 A | 6/1977 | Healy et al. |
| 4,098,836 A | 7/1978 | Dywer |
| 5,329,061 A | 7/1994 | Swift |
| 5,498,822 A | 3/1996 | Eccli et al. |
| 6,147,272 A | 11/2000 | Mikitenko et al. |
| 6,149,874 A | 11/2000 | Hotier |
| 6,180,550 B1 | 1/2001 | Beck et al. |
| 6,448,459 B1 | 9/2002 | Magne-drisch et al. |
| 6,600,083 B2 | 7/2003 | Doyle et al. |
| 6,660,896 B1 | 12/2003 | Buchanan |
| 6,872,866 B1 | 3/2005 | Nemeth et al. |
| 7,244,409 B2 | 7/2007 | Burgfels et al. |
| 7,368,620 B2 | 5/2008 | Zhou |
| 7,371,913 B2 | 5/2008 | Bauer |
| 7,495,137 B2 | 2/2009 | Zhou et al. |
| 7,592,499 B2 | 9/2009 | Wolff et al. |
| 8,221,707 B2 | 7/2012 | Bauer |
| 8,273,934 B2 | 9/2012 | Ou et al. |
| 8,697,929 B2 | 4/2014 | Ou et al. |
| 9,302,201 B2 | 4/2016 | Porter et al. |
| 9,890,094 B2 | 2/2018 | Kuzmanich et al. |
| 2011/0263918 A1 | 10/2011 | Ou et al. |
| 2011/0319688 A1 | 12/2011 | Ou |
| 2015/0175507 A1 | 6/2015 | Bender et al. |
| 2016/0257631 A1 | 9/2016 | Kuzmanich et al. |
| 2017/0297977 A1 | 10/2017 | Bambal et al. |

FOREIGN PATENT DOCUMENTS

| | | |
|---|---|---|
| EP | 0065364 | 11/1982 |
| EP | 0065364 B1 | 12/1984 |
| WO | 2004/094349 A1 | 11/2004 |
| WO | 2011/133326 A2 | 10/2011 |
| WO | 2013/032630 A2 | 3/2013 |
| WO | 2013/085681 A1 | 6/2013 |
| WO | 2014/035626 A1 | 3/2014 |
| WO | 2014/150875 A1 | 9/2014 |
| WO | 2016/175898 A1 | 11/2016 |
| WO | 2017/180509 A1 | 10/2017 |
| WO | 2021/041021 A1 | 3/2021 |

*Primary Examiner* — Thuan D Dang

(57) ABSTRACT

A liquid phase isomerization process comprising cofeeding molecular hydrogen at a feeding rate ≥100 ppm by weight can effectively convert a C8 aromatic hydrocarbon isomerization feed in the presence of an isomerization catalyst with a very low deactivation rate of the catalyst, even at high WHSV ≥5 hour$^{-1}$.

25 Claims, 6 Drawing Sheets

PROCESSES FOR ISOMERIZING C8 AROMATIC HYDROCARBONS

CROSS-REFERENCE TO RELATED APPLICATIONS

This application is a US national phase application of PCT Application Serial No. PCT/US2020/045725 having a filing date of Aug. 11, 2020, which claims priority to and the benefit of U.S. Provisional Application No. 62/890,935 having a filing date of Aug. 23, 2019 and European Patent Application No. 19209114.8 having a filing date of Nov. 14, 2019, the disclosures of all of which are incorporated herein by reference in their entireties.

FIELD

This disclosure relates to isomerization of C8 aromatic hydrocarbons. In particular, this disclosure relates to isomerization of C8 aromatic hydrocarbons under conditions where a majority of the C8 aromatic hydrocarbons are present in liquid phase. This disclosure is useful in, e.g., processes for producing p-xylene.

BACKGROUND

A high purity p-xylene product is typically produced by separating p-xylene from a p-xylene-rich aromatic hydrocarbon mixture comprising p-xylene, o-xylene, m-xylene, and optionally ethylbenzene ("EB") in a p-xylene separation/recovery system. The p-xylene recovery system can comprise, e.g., a crystallizer and/or an adsorption chromatography separating system known in the prior art. The p-xylene-depleted stream produced from the p-xylene recovery system (the "filtrate" from a crystallizer upon separation of the p-xylene crystals, or the "raffinate" from the adsorption chromatography separating system, collectively "raffinate" in this disclosure) is rich in m-xylene and o-xylene, and contains p-xylene at a concentration typically below its concentration in an equilibrium mixture consisting of m-xylene, o-xylene, and p-xylene. To increase yield of p-xylene, the raffinate stream may be fed into an isomerization unit, where the xylenes undergo isomerization reactions in contacting an isomerization catalyst system to produce an isomerized effluent rich in p-xylene compared to the raffinate. At least a portion of the isomerized effluent, after optional separation and removal of lighter hydrocarbons that may be produced in the isomerization unit, can be recycled to the p-xylene recovery system, forming a "xylenes loop."

Xylenes isomerization can be carried out under conditions where the C8 aromatic hydrocarbons are substantially in vapor phase in the presence of an isomerization catalyst (vapor-phase isomerization, or "VPI").

Newer generation technology have been developed to allow xylenes isomerization at significantly lower temperature in the presence of an isomerization catalyst, where the C8 aromatic hydrocarbons are substantially in liquid phase (liquid-phase isomerization, or "LPI"). The use of LPI vs. traditional VPI can reduce the number of phase changes (liquid to/from vapor) required to process the C8 aromatic feed. This provides the process with sustainability advantages in the form of significant energy savings. It would be highly advantageous for any p-xylene production plant to deploy a LPI unit, in addition to or in lieu of a VPI unit. For existing p-xylene production facilities lacking a LPI, it would be highly advantageous to add a LPI unit to compliment the VPI unit or replace the VPI unit.

Exemplary LPI processes and catalyst systems useful therefor are described in U.S. Patent Application Publication Nos. 2011/0263918 and 2011/0319688, 2017/0297977, 2016/0257631, and U.S. Pat. No. 9,890,094, the contents of all of which are incorporated herein by reference in their entirety. In the LPI processes described in these references, typically a MFI framework type zeolite (e.g., ZSM-5) is used as the catalyst.

Due to the many advantages of a LPI process and needs to deploy this technology, improvements in this technology, are also needed. It has been found that the LPI catalyst can experience aging over time with various deactivation rate especially at a high weight hourly space velocity ("WHSV"). It would be highly desirable that in the LPI process, the deactivation of the catalyst is reduced to enable a long catalyst service life and hence a reduced cost for catalyst regeneration and replacement.

This disclosure satisfies this and other needs.

SUMMARY

It has been found that by co-feeding molecular hydrogen at a high feeding rate of at least 100 ppm along with a liquid phase of a C8 aromatic hydrocarbon feed, one can significantly reduce the deactivation of the isomerization catalyst in a LPI process, even at high WHSV of at least 5 hour$^{-1}$, and even at least 20 hour$^{-1}$.

Thus, a first aspect of this disclosure relates to a process comprising: feeding molecular hydrogen and a liquid phase isomerization hydrocarbon feed comprising C8 aromatic hydrocarbons into an isomerization reactor having an isomerization catalyst disposed therein, wherein the molecular hydrogen is fed at a feeding rate from 100 ppm to 5000 ppm by weight, based on the total weight of the isomerization hydrocarbon feed; and contacting the molecular hydrogen and the C8 aromatic hydrocarbons with the isomerization catalyst under isomerization conditions in the isomerization reactor to produce an isomerization effluent, wherein the isomerization conditions comprise a reaction pressure in the isomerization reactor from 1,700 kPa-gauge to 3,500 kPa-gauge and a reaction temperature such that the C8 aromatic hydrocarbons are substantially in liquid phase in the isomerization reactor, and a weight hourly space velocity from 5 hour$^{-1}$ to 20 hour$^{-1}$.

A second aspect of this disclosure relates to a process for producing p-xylene, the process comprising: feeding molecular hydrogen and a liquid phase isomerization hydrocarbon feed comprising C8 aromatic hydrocarbons into an isomerization reactor having an isomerization catalyst disposed therein, wherein the molecular hydrogen is fed at a feeding rate from 100 ppm to 5000 ppm by weight, based on the total weight of the isomerization hydrocarbon feed; and contacting the molecular hydrogen and the C8 aromatic hydrocarbons with the isomerization catalyst under isomerization conditions in the isomerization reactor to produce an isomerization effluent, wherein the isomerization conditions comprise a reaction pressure from 1,700 kPa-gauge to 3,500 kPa-gauge and a reaction temperature of from 200 to 300° C. such that the C8 aromatic hydrocarbons are substantially in liquid phase in the isomerization reactor, and a weight hourly space velocity from 5 hour$^{-1}$ to 20 hour$^{-1}$; the isomerization effluent comprises p-xylene at a concentration higher than the isomerization hydrocarbon feed; and recovering at least a portion of the p-xylene from the isomerization effluent.

DETAILED DESCRIPTION

Figure 1:
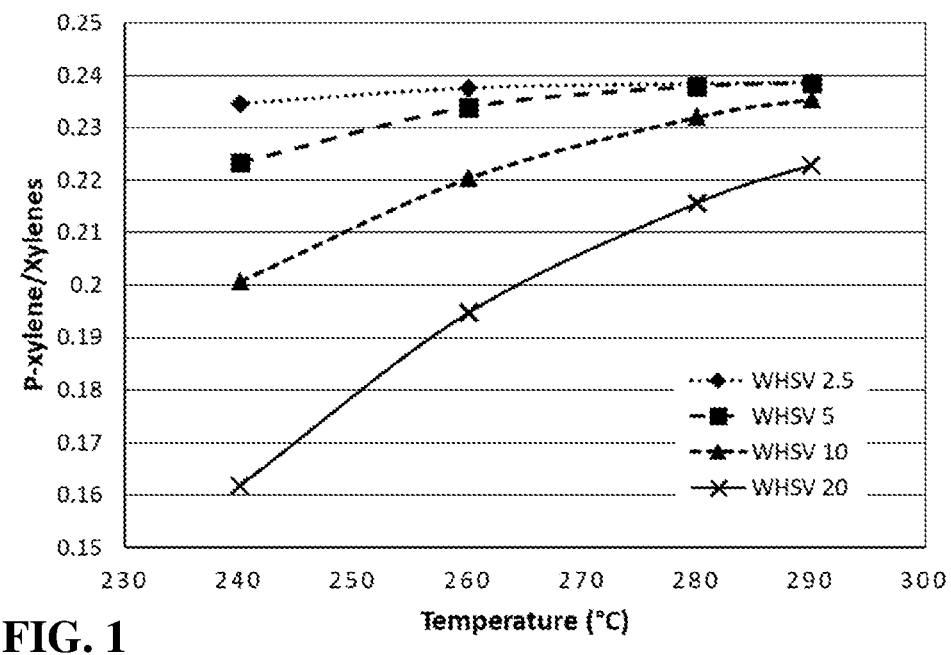
FIG. 1 is a graph showing p-xylene/xylenes as a function of reaction temperature at various WHSV in simulated LPI processes of this disclosure.

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In this disclosure, a process is described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a fractionation column" include embodiments where one, two or more fractionation columns are used, unless specified to the contrary or the context clearly indicates that only one fractionation column is used.

"Consisting essentially of" as used herein means the composition, feed, or effluent comprises a given component at a concentration of at least 60 wt %, preferably at least 70 wt %, more preferably at least 80 wt %, more preferably at least 90 wt %, still more preferably at least 95 wt %, based on the total weight of the composition, feed, or effluent in question.

"Substantially entirely" means at least 95 wt %, preferably ≥98 wt %, preferably ≥99 wt %, preferably ≥99.5 wt %, preferably ≥99.9 wt %. Thus, where C8 aromatic hydrocarbons are present in a reactor substantially entirely in liquid phase, at least 95 wt %, preferably ≥98 wt %, preferably ≥99 wt %, preferably ≥99.5 wt %, preferably ≥99.9 wt %, of such C8 aromatic hydrocarbons are present in the reactor in liquid phase. Where molecular hydrogen is dissolved substantially entirely in an isomerization hydrocarbon feed in liquid phase, at least 95 wt %, preferably ≥98 wt %, preferably ≥99 wt %, preferably ≥99.5 wt %, preferably ≥99.9 wt %, of such molecular hydrogen is dissolved in the isomerization hydrocarbon feed in liquid phase.

The term "hydrocarbon" means (i) any compound consisting of hydrogen and carbon atoms or (ii) any mixture of two or more such compounds in (i). The term "Cn hydrocarbon," where n is a positive integer, means (i) any hydrocarbon compound comprising carbon atom(s) in its molecule at the total number of n, or (ii) any mixture of two or more such hydrocarbon compounds in (i). Thus, a C2 hydrocarbon can be ethane, ethylene, acetylene, or mixtures of at least two of them at any proportion. A "Cm to Cn hydrocarbon" or "Cm-Cn hydrocarbon," where m and n are positive integers and m<n, means any of Cm, Cm+1, Cm+2, . . . , Cn−1, Cn hydrocarbons, or any mixtures of two or more thereof. Thus, a "C2 to C3 hydrocarbon" or "C2-C3 hydrocarbon" can be any of ethane, ethylene, acetylene, propane, propene, propyne, propadiene, cyclopropane, and any mixtures of two or more thereof at any proportion between and among the components. A "saturated C2-C3 hydrocarbon"

can be ethane, propane, cyclopropane, or any mixture thereof of two or more thereof at any proportion. A "Cn+ hydrocarbon" means (i) any hydrocarbon compound comprising carbon atom(s) in its molecule at the total number of at least n, or (ii) any mixture of two or more such hydrocarbon compounds in (i). A "Cn-hydrocarbon" means (i) any hydrocarbon compound comprising carbon atoms in its molecule at the total number of at most n, or (ii) any mixture of two or more such hydrocarbon compounds in (i). A "Cm hydrocarbon stream" means a hydrocarbon stream consisting essentially of Cm hydrocarbon(s). A "Cm-Cn hydrocarbon stream" means a hydrocarbon stream consisting essentially of Cm-Cn hydrocarbon(s).

"Light hydrocarbon" in this disclosure means any C5-hydrocarbon.

"Liquid-phase isomerization" and "LPI" interchangeably mean a C8 aromatic hydrocarbon isomerization process in an isomerization zone in the presence of an isomerization catalyst whereby the xylenes isomerize under isomerization conditions such that the C8 aromatic hydrocarbons present in the isomerization zone are substantially in liquid phase. "Substantially in liquid phase" means ≥80 wt %, preferably ≥85 wt %, preferably ≥90 wt %, preferably ≥95 wt %, preferably ≥99 wt %, preferably the entirety, are in liquid phase. Such isomerization conditions are called liquid-phase isomerization conditions.

"Vapor-phase isomerization" and "VPI" interchangeably mean a C8 aromatic hydrocarbon isomerization process in an isomerization zone in the presence of an isomerization catalyst whereby the xylenes isomerize under isomerization conditions such that the xylenes present in the isomerization zone are substantially in vapor phase. "Substantially in vapor phase" means ≥90 wt %, preferably ≥95 wt %, preferably ≥99 wt %, preferably the entirety, is in vapor phase. Such isomerization conditions are called vapor-phase isomerization conditions.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All concentrations herein are expressed on the basis of the total amount of the composition in question. All ranges expressed herein should include both end points as two specific embodiments unless specified or indicated to the contrary.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, 6th Edition, by F. Albert Cotton et al. (John Wiley & Sons, Inc., 1999).

The processes of this disclosure can be used for making a p-xylene product comprising p-xylene at a high concentration, and/or an o-xylene product comprising o-xylene at a high concentration, and/or an m-xylene product comprising m-xylene at a high concentration. Given the higher economic value of p-xylene and o-xylene over m-xylene, the processes of this disclosure are preferably used for making p-xylene and/or o-xylene products, more preferably a p-xylene product. In typical C8 aromatic hydrocarbon isomerization processes, a C8 aromatic hydrocarbon feed comprising the xylenes at non-equilibrium concentrations are contacted with an isomerization catalyst in an isomerization reactor under isomerization conditions for a period of time to effect the conversion of the xylenes to produce an isomerization effluent exiting the isomerization reactor comprising the xylenes at concentrations closer to their equilibrium concentrations. Thus, for the purpose of producing a p-xylene product, the C8 aromatic hydrocarbon feed fed into the isomerization reactor typically comprises (i) p-xylene at a concentration based on the total quantity of xylenes in the isomerization hydrocarbon feed significantly lower than its equilibrium concentration in a xylenes mixture, and (ii) o-xylene and m-xylene at a combined concentration based on the total quantity of xylenes in the isomerization hydrocarbon feed significantly higher than their combined equilibrium concentrations. On contacting the isomerization catalyst in the isomerization reactor under the isomerization conditions, a portion of the m-xylene and/or o-xylene is converted into p-xylene to produce an isomerization effluent comprising p-xylene at a higher concentration thereof based on the total quantity of the xylenes in the effluent. It is highly desired that the p-xylene concentration based on the total quantity of xylenes in the isomerization effluent is close to its equilibrium concentration in a xylenes mixture. The increased amount of p-xylene in the effluent can be recovered to produce a p-xylene product. A "xylenes mixture" means a mixture consisting of p-xylene, m-xylene, and o-xylene.

The processes of this disclosure comprises a LPI step with co-feeding of a significant quantity of molecular hydrogen into the isomerization reactor. It has been surprisingly found that the presence of such significant amount of molecular hydrogen can significantly reduce the deactivation rate of the LPI catalyst, even at a high WHSV ≥5.0, ≥7.5, ≥10, ≥12.5, ≥15, ≥17.5, and even ≥20 hour$^{-1}$.

Various embodiments of the processes of this disclosure comprise introducing a feed comprising C8 hydrocarbons and molecular hydrogen into a reactor having a xylene isomerization catalyst disposed therein, wherein the isomerization hydrocarbon feed comprises 100 ppm to 5000 ppm by weight of the molecular hydrogen based on the total weight of the isomerization hydrocarbon feed, and reacting the isomerization hydrocarbon feed substantially in liquid phase in the presence of the xylene isomerization catalyst to produce an isomerization effluent having an increased concentration of para-xylene relative to a concentration of para-xylene in the isomerization hydrocarbon feed, wherein the isomerization hydrocarbon feed contacts the xylene isomerization catalyst under a gauge pressure of about 1,700 kPa to about 3,500 kPa at a weight hour space velocity of about 5 hour$^{-1}$ to about 20 hour$^{-1}$.

The Isomerization Hydrocarbon Feed Comprising C8 Aromatic Hydrocarbon in the Processes of this Disclosure The isomerization hydrocarbon feed comprising C8 aromatic hydrocarbon to the isomerization reactor can comprise one of the more of the xylenes at various concentrations. For example, the isomerization hydrocarbon feed can comprise xylenes at a total concentration from c(xylenes)1 to c(xylenes)2 wt %, based on the total weight of the isomerization hydrocarbon feed, where c(xylenes)1 and c(xylenes)2 can be, independently, 30, 40, 50, 55, 60, 65, 70, 75, 80, 85, 90, 91, 92, 93, 94, 95, 96, 97, 98, 99, or even 100, as long as c(xylenes)1<c(xylenes)2. Preferably c(xylenes)1=70. More preferably c(xylenes)1=80. Preferably the isomerization hydrocarbon feed consists essentially of the xylenes.

The isomerization hydrocarbon feed can comprise ethylbenzene at various concentrations, e.g., from c(EB)1 to c(EB)2 wt %, based on the total weight of the isomerization hydrocarbon feed, where c(EB)1 and c(EB)2 can be, independently, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, as long as c(EB)1<c(EB)2. Preferably C(EB)2=20. Preferably C(EB)2=10. Preferably C(EB)2=5.

For the purpose of producing a p-xylene product, it is highly desirable that the isomerization hydrocarbon feed comprising C8 aromatic hydrocarbons to the isomerization zone comprises p-xylene at a concentration based on the total quantity of xylenes in the isomerization hydrocarbon feed lower than the concentration thereof in an equilibrium xylenes mixture. Thus p-xylene in the isomerization hydrocarbon feed can have a concentration c(pX) based on the total quantity of the xylenes in the isomerization hydrocarbon feed ranging from c(pX)1 to c(pX)2 wt %, where c(pX)1 and c(pX)2 can be, independently, e.g., 0, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, as long as c(pX)1<c(pX)2. Preferably c(pX)2=20. Preferably c(pX)2=15. Preferably c(pX)2=12. Preferably c(pX)2=10. Preferably c(pX)2=8. Preferably c(pX)2=6. Preferably c(pX)2=5. Preferably c(pX)2=4. Preferably c(pX)2=2. Preferably c(pX)2=1. m-Xylene in the isomerization hydrocarbon feed can have a concentration c(mX) based on the total quantity of the xylenes in the isomerization hydrocarbon feed ranging from c(mX)1 to c(mX)2 wt %, where c(mX)1 and c(mX)2 can be, independently, e.g., 10, 15, 20, 25, 30, 35, 40, 45, 50, 55, 60, 65, 70, 75, 80, 85, 90, 95, as long as c(mX)1<c(mX)2. Preferably c(mX)1=30 and c(mX)2=80. Preferably c(mX)1=40, and c(mX)2=80. o-Xylene in the isomerization hydrocarbon feed can have a concentration c(oX) based on the total quantity of the xylenes in the isomerization hydrocarbon feed ranging from c(oX)1 to c(oX)2 wt %, where c(oX)1 and c(oX)2 can be, independently, e.g., 10, 15, 20, 25, 30, 35, 40, 45, 50, 55, 60, 65, 70, 75, 80, 85, 90, 95, as long as c(oX)1<c(oX)2. Preferably c(oX)1=10 and c(oX)2=80. Preferably c(oX)1=10, and c(oX)2=60. Preferably c(oX)1=10, and c(oX)2=50. Preferably c(oX)1=15, and c(oX)2=30. Such feed can be a raffinate stream exiting a p-xylene recovery sub-system, e.g., one using adsorption chromatography-based separation technology.

The isomerization hydrocarbon feed may comprise benzene, toluene, and C9+ hydrocarbons, but desirably at low quantities. The isomerization hydrocarbon feed may comprise benzene and toluene combined in a range from c(BT)1 to c(BT)2 wt %, based on the total weight of the isomerization hydrocarbon feed, where c(BT)1 and c(BT)2 can be, independently, e.g., 0.01, 0.1, 1.0, 2.0, 3.0, 5.0, 8.0, 10.0, 15.0, 20.0, as long as c(BT)1<c(BT)2. Preferably c(BT)2=10.0. Preferably c(BT)2=5.0. Preferably c(BT)2=3.0. Toluene can be the primary component between benzene and toluene. For example, the isomerization hydrocarbon feed can be substantially free of benzene. The isomerization hydrocarbon feed may comprise C9+ hydrocarbons, in total, in a range from c(C9+)1 to c(C9+)2 wt %, based on the total weight of the isomerization hydrocarbon feed, where c(C9+)1 and c(C9+)2 can be, independently, e.g., 0.01, 0.1, 1.0, 5.0, 10.0, 20.0, as long as c(C9+)1<c(C9+)2.

In various embodiments of the processes of this disclosure, at least 80 wt %, preferably ≥85 wt %, preferably ≥90 wt %, preferably 95 wt %, preferably ≥98 wt %, preferably ≥99 wt %, preferably approximately 100 wt %, of the isomerization hydrocarbon feed comprising the C8 aromatic hydrocarbons is in liquid phase at the inlet to the isomerization reactor. The isomerization hydrocarbon feed can have an inlet temperature in the range from T1 to T2° C., where T1 and T2 can be, independently, e.g., 200, 210, 220, 230, 240, 250, 255, 260, 265, 270, 275, 280, 285, 290, 295, 300, as long as T1<T2. The relatively low inlet temperature of the isomerization hydrocarbon feed, in combination with other isomerization conditions such as pressure described below, enables an LPI process inside the isomerization reactor.

The Molecular Hydrogen Co-Feed

Certain LPI processes in the prior art were conducted in the absence of co-feeding molecular hydrogen into the isomerization zone. We have found that in the absence of co-feeding any molecular hydrogen into the reactor, the isomerization catalyst can deactivate overtime at a relatively fast pace, especially at a high WHSV≥5 hour$^{-1}$. In cases where molecular hydrogen is supplied into the isomerization reactor at a low feeding rate, e.g., at ≤10 ppm by weight, based on the total weight of the aromatic hydrocarbon feed into the reactor, the isomerization catalyst may deactivate at a pace which, compared to no co-feeding of molecular hydrogen at all, is lower, but nonetheless can be appreciable. Isomerization catalyst deactivation at an appreciable pace can be observed at low feeding rate of molecular hydrogen or in the absence of co-feeding molecular hydrogen even in cases where the isomerization hydrocarbon feed is relatively easy to isomerize, e.g., where the isomerization feed comprises p-xylene at a high concentration (e.g., ≥5 wt %, ≥8 wt %, ≥10 wt %, based on the total weight of the xylenes) and/or the isomerization feed comprises ethylbenzene at a low concentration (e.g., ≤8 wt %, ≤6 wt %, ≤5 wt %, ≤4 wt %, ≤2 wt %).

When molecular hydrogen is co-fed at a high feeding rate of ≥100 ppm by weight pursuant to this disclosure, based on the total weight of the isomerization hydrocarbon feed comprising C8 aromatic hydrocarbon feed, the deactivation rate of the isomerization catalyst can be reduced significantly compared to both (i) no co-feeding of molecular hydrogen at all and (ii) co-feeding molecular hydrogen at a low rate, e.g., at ≤10 ppm by weight. In a totally unexpected manner, the low deactivation rate with co-feeding of molecular hydrogen at ≥100 ppm was observed even at high WHSV≥5 hour$^{-1}$, ≥7.5 hour$^{-1}$, ≥10 hour$^{-1}$, ≥12.5 hour$^{-1}$, ≥15 hour$^{-1}$, ≥17.5 hour$^{-1}$, and even ≥20 hour$^{-1}$.

In certain embodiments, the molecular hydrogen co-fed into the isomerization reactor, or a portion thereof, can be injected into the isomerization reactor via an inlet as a pressurized gas. Additionally or alternatively, the molecular hydrogen or a portion thereof can be fed into a feeding line, a vessel, or a storage tank of the isomerization hydrocarbon feed comprising the C8 aromatic hydrocarbons, where it forms a mixture with the isomerization hydrocarbon feed, which is then supplied into the isomerization reactor. It is highly desired that a portion, preferably a majority (e.g., ≥50%, ≥60%, ≥70%, ≥80%, ≥90%, ≥95%, ≥98%), more preferably substantially the entirety (≥99%), of the co-fed molecular hydrogen is dissolved in the liquid phase in the isomerization reactor. To achieve a higher concentration of dissolved molecular hydrogen in the liquid phase of the isomerization hydrocarbon feed, a higher pressure can be applied. To maintain a substantial portion of the molecular hydrogen dissolved in the liquid phase in the isomerization reactor, it is highly desired that the feeding rate of molecular hydrogen into the isomerization reactor be no higher than 5000 ppm by weight, based on the total weight of the isomerization hydrocarbon feed. Approximate solubility of molecular hydrogen in liquid-phase C8 aromatic hydrocarbons in ppm by weight, based on the total weight of the C8 aromatic hydrocarbons, at 25° C. at various pressures is given in TABLE I below:

TABLE I

| Pressure (gauge) | (kPa) | 1378 | 1724 | 2068 | 2413 | 2758 | 3447 |
|---|---|---|---|---|---|---|---|
|  | (psi) | 200 | 250 | 300 | 350 | 400 | 500 |
| $H_2$ Solubility | (ppm) | 107 | 132 | 157 | 181 | 206 | 255 |

Thus, the molecular hydrogen can be fed into the isomerization reactor at a feeding rate of r(H2)1 to r(H2)2 ppm by weight, based on the total weight of the isomerization hydrocarbon feed, where r(H2)1 and r(H2)2 can be, independently, e.g., 100, 150, 200, 250, 300, 350, 400, 450, 500, 550, 600, 650, 700, 750, 800, 850, 950, 1000, 1500, 2000, 2500, 3000, 3500, 4000, 4500, 5000, as long as r(H2)1<r(H2)2. Preferably r(H2)2=3000. Preferably r(H2)2=2000. Preferably r(H2)2=1000. Preferably r(H2)2=800. Preferably r(H2)2=600. Preferably r(H2)2=500.

The molecular hydrogen, if premixed with the isomerization hydrocarbon feed, will be fed into the isomerization reactor at an inlet temperature as discussed above. If fed separately from the isomerization hydrocarbon feed, it may be fed into the isomerization reactor as a stream gas at an inlet temperature preferably in proximity to the inlet temperature of the isomerization hydrocarbon feed, at a pressure sufficient to enable its dissolution in the liquid phase in the isomerization reactor to effect LPI in the isomerization reactor.

The LPI Conditions

The LPI step in the processes of this disclosure is conducted in an LPI reactor in the presence of an LPI catalyst under LPI conditions.

The LPI conditions can include a reaction gauge pressure in the isomerization reactor ranging from p1 to p2 kPa, where p1 and p2 can be, independently, e.g., 1700, 1800, 1900, 2000, 2100, 2200, 2300, 2400, 2500, 2600, 2700, 2800, 2900, 3000, 3100, 3200, 3300, 3400, 3500, as long as p1<p2. Preferably p2=3000. Preferably p2=2500. The higher the reaction pressure, the larger the quantity of molecular hydrogen can be dissolved in the liquid phase of the hydrocarbons present in the reactor, as indicated above.

The LPI conditions can include a reaction temperature in the isomerization reactor ranging from T1 to T2° C., where T1 and T2 can be, independently, e.g., 200, 210, 220, 230, 240, 250, 255, 260, 265, 270, 275, 280, 285, 290, 295, 300, as long as T1<T2. The relatively low reaction temperature of the LPI processes can be particularly energy efficient because it requires less energy to heat the isomerization hydrocarbon feed, and it does not require condensing a large quantity of high-temperature vapor-phase isomerization effluent into liquid for downstream processing.

The LPI conditions in the processes of this disclosure can particularly advantageously include a high WHSV ranging from w1 to w2 hour$^{-1}$, where w1 and w2 can be, e.g., 5.0, 5.5, 6.0, 6.5, 7.0, 7.5, 8.0, 8.5, 9.0, 9.5, 10, 11, 12, 12.5, 13, 14, 15, 16, 17, 17.5, 18, 19, 20, as long as w1<w2. As indicated above and demonstrated in the comparative examples below, LPI processes without co-feeding molecular hydrogen or with co-feeding molecular hydrogen at a low feeding rate can experience catalyst deactivation at a high rate, even at a WHSV of 4 hour$^{-1}$. Such high WHSV of the processes of this disclosure enables compact LPI reactor design for a new LPI with a given capacity, increased capacity for an existing LPI reactor with a given catalyst load, and reduced catalyst consumption for the production of a given quantity of p-xylene product.

In certain embodiments of the processes of this disclosure, one can increase the reaction temperature and/or weight hourly space velocity without substantially decreasing the p-xylene/xylenes weight ratio in the isomerization effluent. "Substantially decreasing the same p-xylene/xylenes weight ratio" means decreasing the p-xylene/xylenes weight ratio in the isomerization effluent by ≥10% based on the p-xylene/xylenes weight ratio before increasing the reaction temperature and/or the weight hourly space velocity. "p-xylene/xylenes" weight ratio means the weight ratio of p-xylene to all xylenes present in a mixture or stream.

In certain other embodiments of the processes of this disclosure, one can increase the reaction temperature and/or the weight hourly space velocity without substantially increasing the xylenes loss in the process. "Substantially increasing the xylenes loss" means increasing the xylenes loss by ≥10% based on the xylenes loss before increasing the reaction temperature and/or the weight hourly space velocity. "Xylenes loss" means the concentration of all xylenes present in an effluent stream minus the concentration of all xylenes present in the feed, in weight percentage.

In certain other embodiments of the processes of this disclosure, one can feed the molecular hydrogen at the beginning phase of a catalyst cycle at a first rate, and then subsequently during normal operation of the isomerization reactor at a second rate, where the first rate is lower than the second rate. The beginning phase of a catalyst cycle means the period of a catalyst cycle when the catalyst demonstrates an exceedingly high activity which can result in side-reactions and over-production of byproducts. For example, in the beginning phase, the molecular hydrogen can be fed into reactor at a rate from 0 to 500, or from 0 to 300, or from 0 to 200, or from 0 to 150 ppm. At a low first feeding rate of the molecular hydrogen, the isomerization catalyst is allowed to deactivate ("de-edge") at a relatively high rate to reduce the side-reaction and the production of byproducts. At the end of the beginning phase, where de-edging of the isomerization catalyst is complete, the molecular hydrogen feeding rate can be increased to a higher level to reduce the deactivation of the isomerization catalyst to a desired level.

The Isomerization Catalyst

U.S. Pat. Nos. 6,180,550, 6,448,459, 6,872,866, 7,244,409, 7,371,913, 7,495,137, 7,592,499, 8,221,707, 8,273,934, and 8,697,929 describe LPI processes and/or catalysts suitable for aromatic hydrocarbon isomerization processes, the relevant portions of which are incorporated herein by reference in their entirety. Any suitable LPI catalysts known in the art may be used in the processes of this disclosure.

The isomerization catalyst useful in the LPI step of the processes of this disclosure can comprise a molecular sieve such as a zeolite. Such zeolite can be selected from, but are not limited to, zeolites having the following framework structures, and combinations thereof: MFI, MEL, MWW, MOR, and the like. Preferably, the isomerization catalyst comprises a MFI framework zeolite such as ZSM-5. Preferably, the isomerization catalyst comprises a zeolite having a 10- or 12-member ring structure such as a MWW or MOR framework zeolite, or a mixture thereof. Preferably, the isomerization catalyst comprises both a first zeolite having a MFI framework structure such as ZSM-5, and a second zeolite differing from the first zeolite having a10- or 12-member ring structure. Non-limiting examples of MWW zeolites useful for the isomerization catalyst used in the processes of this disclosure include: MWW-22, MWW-49, MWW-54, and combinations thereof. The zeolites present in the isomerization catalyst may be advantageously in the hydrogen form. The following combinations of zeolites are particularly advantageous for the isomerization catalyst: ZSM-5 and MWW-22; ZSM-5 and MWW-49; and ZSM-5 and MWW-56.

In certain embodiments, the isomerization catalyst can comprise a first metal element selected from Fe, Co, Ni, Ru, Rh, Pd, Re, Os, Ir, Pt, and combinations thereof, and optionally a second metal selected from Sn, Zn, Ag, and combinations thereof. The first metal element may catalyze hydrogenation of olefins that may be produced in the isomerization reactions by, e.g., dealkylation of ethylbenzene. The second metal element may promote the catalytic effect of the first metal element. In other embodiments, the isomerization catalyst is free of precious metal (i.e., Ru, Rh, Pd, Os, Ir, and Pt). In other embodiments, the isomerization catalyst may be free of any Group 7-10 metal. In other embodiments, the isomerization catalyst may be free of any Group 7-15 metals except aluminum.

The ZSM-5 zeolite useful for the isomerization catalyst can have one or more of the following characteristics: in the hydrogen form (HZSM-5); having a crystal size ≤0.1 micron; having a mesoporous surface area (MSA) ≥45 m$^2$/g; a total surface area to mesoporous surface area ratio ≤9; and a silica to alumina molar ratio in the range of 20 to 50.

The isomerization catalyst may be a self-bound zeolite catalyst substantially free of a binder. Alternatively, the isomerization catalyst can comprise, in addition to the molecular sieves such as zeolites, a binder material. Examples of suitable binder materials include, but are not limited to: alumina, silica, aluminosilicate, zirconia, zircon, titania, clay (e.g., montmorillonite, bentonite, subbentonite), kaolin (e.g., Dixie, McNamee, Georgia and Florida clays or others in which the main mineral constituent is halloysite, kaolinite, nacrite or anauxite), combinations thereof, chemical compounds thereof, and the like. Any suitable quantity of binder may be present in the isomerization catalyst. For example, the binder material may be included in the isomerization catalyst at a concentration from c1 to c2 wt %, based on the total weight of the catalyst, where c1 and c2 can be, independently, 1, 5, 10, 15, 20, 25, 30, 35, 40, 45, 50, 55, 60, 65, 70, 75, 80, 85, 90, 95, 98, 99, as long as c1<c2. The inclusion of a binder in the isomerization catalyst can enhance its mechanical strength, among others.

The isomerization catalyst can be made by processes known in the art. For example, components of the catalyst such as the zeolite and the optional binder can be admixed to form an intimate mixture, which is then extruded to desired shape, dried, calcined, and optionally selectivated to produce the isomerization catalyst. A raw catalyst may be activated in the isomerization reactor or outside of the reactor before the C8 aromatic hydrocarbon isomerization operation. Activation can be conducted by, e.g., exposing the catalyst to a stream of molecular-hydrogen-containing gas.

The isomerization catalyst may be a freshly made catalyst or a regenerated catalyst, or a mixture thereof. Regeneration of the catalyst may be conducted in the isomerization reactor after the catalyst activity has decreased to a threshold level at the end of catalyst cycle by, e.g., exposing the catalyst to a stream of molecular hydrogen-containing gas. Alternatively, ex situ regeneration of the catalyst may be implemented, where the spent catalyst is taken out of the isomerization reactor, heated in an oxygen-rich environment and/or exposed to a molecular hydrogen-containing gas stream to abate coke on its surface.

In some embodiments, the reactor can be a fixed bed reactor, a fluidized bed reactor, or a moving bed reactor. The hydrocarbon liquid in the reactor can flow upward, downward, or in a radial fashion.

The Isomerization Effluent

As a result of the isomerization reactions in the reactor, the isomerization effluent desirably comprises p-xylene at a concentration higher than in the isomerization hydrocarbon feed, and m-xylene and o-xylene at a combined concentration lower than in the isomerization hydrocarbon feed. The isomerization effluent may comprise p-xylene at a concentration of from c(pX)1 to c(pX)2 wt %, based on the total weight of the xylenes in the isomerization effluent, where c(pX)1 and c(pX)2 can be, independently, e.g., 15, 16, 17, 18, 19, 20, 21, 22, 23, as long as c(pX)1<c(pX)2. Preferably c(pX)1=18. Preferably c(pX)1=20. Preferably c(pX)1=21. Preferably c(pX)1=22. Preferably c(pX) is in proximity to its concentration in an equilibrium xylenes mixture at the isomerization temperature. In the processes of this disclosure, by co-feeding molecular hydrogen at a feeding rate ≥100 ppm by weight, based on the total weight of the isomerization hydrocarbon feed, one can achieve a high activity of the isomerization catalyst, enabling and sustaining c(pX)1≥20 wt % for a long period of time, even at high WHSV of ≥5 hour$^{-1}$, ≥7.5 hour$^{-1}$, ≥10 hour$^{-1}$, ≥12.5 hour$^{-1}$, ≥15 hour$^{-1}$, ≥17.5 hour$^{-1}$, and even ≥20 hour$^{-1}$, which is totally surprising.

The isomerization effluent comprises m-xylene and o-xylene at a combined concentration lower than the isomerization feed. Desirably the m-xylene concentration in the isomerization effluent, based on the total weight of the xylenes in the isomerization effluent, is in proximity to its concentration in an equilibrium xylenes mixture. Thus, the isomerization effluent may comprise m-xylene at a concentration of from c(mX)1 to c(mX)2 wt %, based on the total weight of the xylenes in the isomerization effluent, where c(mX)1 and c(mX)2 can be, independently, e.g., 40, 42, 44, 45, 46, 48, 49, 50, 51, 52, 54, 55, 56, 58, 60, 62, 64, 65, 66, 68, 70, as long as c(mX)1<c(mX)2. Preferably c(mX)2=60. Preferably c(mX)2=58. Preferably c(mX)2=55. Preferably c(mX)2=53. Preferably c(mX)2=50. Desirably the o-xylene concentration in the isomerization effluent, based on the total weight of the xylenes in the isomerization effluent, is in proximity to its concentration in an equilibrium xylenes mixture. Thus, the isomerization effluent may comprise o-xylene at a concentration of from c(oX)1 to c(oX)2 wt %, based on the total weight of the xylenes in the isomerization effluent, where c(oX)1 and c(oX)2 can be, independently, e.g., 15, 16, 18, 20, 22, 24, 25, 26, 28, 30, 32, 34, 35, as long as c(oX)1<c(oX)2. Preferably c(oX)1=20 and c(oX)2=30. Preferably c(oX)1=20 and c(oX)2=26.

The isomerization effluent can comprise ethylbenzene at various concentrations, depending on the ethylbenzene concentration present in the isomerization hydrocarbon feed.

Recovery of p-Xylene

The isomerization effluent, rich in p-xylene and depleted in m-xylene and o-xylene combined compared to the isomerization hydrocarbon feed, can be fed into a p-xylene recovery sub-system, from which a high-purity p-xylene product can be produced.

The p-xylene recovery system can utilize an adsorption chromatography process to separate p-xylene from m-xylene, o-xylene, and ethylbenzene present in the isomerization effluent. Exemplary adsorption chromatography process and systems are described in, e.g., U.S. Pat. Nos. 3,040,777, 3,201,491, 3,422,848, 9,302,201, 3,761,533, 4,029,717, 6,149,874, and 9,302,201, the relevant portions thereof are incorporated herein in their entirety.

The p-xylene recovery system can utilize a crystallization process to separate p-xylene from the other C8 aromatic hydrocarbons present in the isomerization effluent. Exemplary crystallization separation processes and systems are described in, e.g., 3,662,013, 5,329,061, 5,498,822, 6,147, 272, and 6,600,083, the relevant portions thereof are incorporated herein in their entirety.

The p-xylene recovery system can utilize a combination of an adsorption chromatography process and a crystallization process as described above.

The p-xylene recovery system can receive, in addition to the isomerization effluent produced from an isomerization reactor in a process of this disclosure, other p-xylene-containing streams, e.g., one or more p-xylene-rich streams produced from a C7–/C9+ aromatic hydrocarbon transalkylation process, a toluene disproportionation process, a benzene/toluene methylation with methanol process, and the like.

The processes of this disclosure utilizes a LPI reactor. In certain embodiments, a single LPI reactor may be sufficient to handle all isomerization hydrocarbon feed. In other embodiments, it may be desirable to use two or more LPI reactors, connected in series and/or in parallel. Where multiple LPI reactors are connected in parallel, they may be configured to have overlapping but different operation cycles, so that when one reactor is shut down for catalyst replacement or repair, the other may continue to operate to ensure the continuity of the operation of other components in the aromatic product complex. Alternatively or additionally, where multiple LPI reactors are connected in series, they may be configured to have overlapping but different operation cycles, so that when one reactor is time for catalyst replacement or repair, the other may be allowed to continue to operate to ensure the continuity of the operation of other components in the aromatic product complex. Where two LPI reactors are connected in series including an upstream reactor (i.e., a lead reactor) and a downstream reactor (i.e., a lag reactor), it is contemplated that the two reactors may be brought online at the same or different times, and the two reactors may switch positions as the lead or lag reactor. It is also contemplated that multiple LPI reactors may be allowed to operate in series for a certain time period, and then in parallel for another time period.

The processes of this disclosure may also include a LPI reactor and a VPI reactor. The LPI reactor is operated under the isomerization conditions as described above. The VPI reactor is operated under VPI conditions to carry out a VPI process conducted in vapor phase in the presence of a VPI catalyst. VPI processes and reactors known in the art may be used. References describing VPI processes and/or reactors and/or catalysts include, but are not limited to: U.S. Pat. Nos. 3,651,162, 3,856,872, 3,919,339, 4,098,836, the relevant portions thereof are incorporated herein by reference in their entirety. The LPI reactor and the VPI reactor may be operated in parallel or in series. Preferably, the LPI reactor and the VPI reactor operate in series. Preferably the LPI is a lead reactor and the VPI reactor is a lag reactor. A VPI reactor can be more effective than an LPI reactor in converting ethylbenzene into useful products such as benzene and/or xylenes. Thus, a combination of an LPI reactor and a VPI reactor can be advantageously used to process an isomerization hydrocarbon feed comprising ethylbenzene at an elevated concentration, e.g., ≥8 wt %, ≥10 wt %, ≥12 wt %, ≥15 wt %, 20 wt %, based on the total weight of the isomerization hydrocarbon feed.

In the following cases (Case Nos. 1-7), description is given to various specific embodiments of the processes of this disclosure. The simulation in Cases 1-5 are applicable for LPI processes with cofeeding molecular hydrogen into the LPI reactor pursuant to embodiments of this disclosure, and similarly for LPI processes without cofeeding molecular hydrogen into the isomerization reactor.

Figure 2:
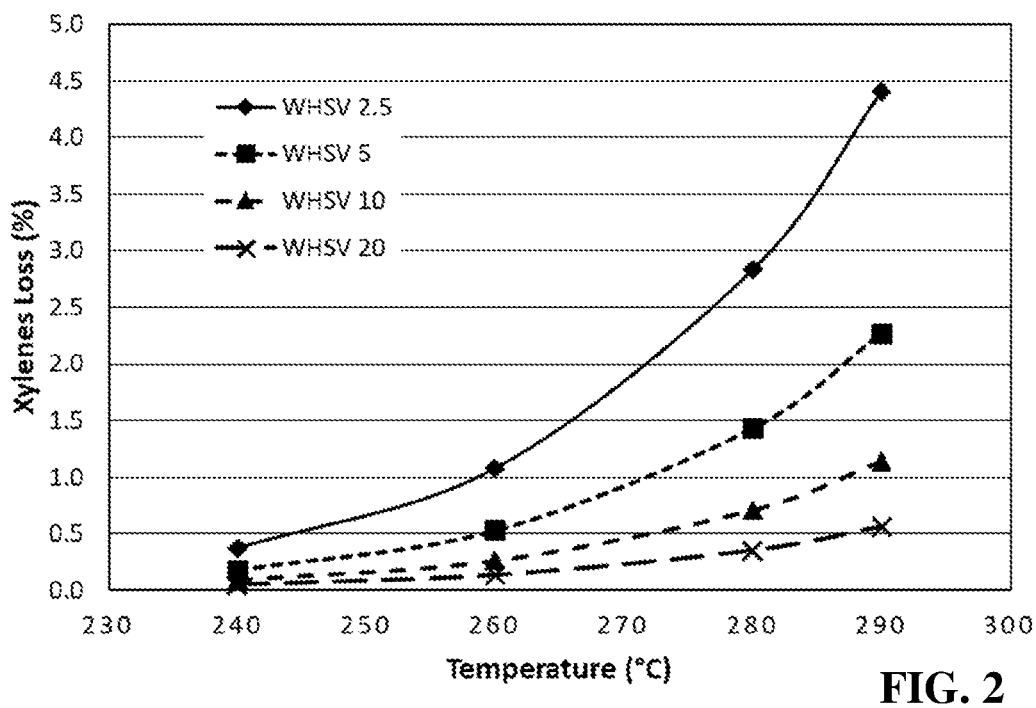
FIG. 2 is a graph showing xylenes loss as a function of reaction temperature at various WHSV in simulated LPI processes of this disclosure.

Case 1: Manipulating Temperature to Minimize Catalyst Load Size while Optimizing Extent of Xylene Isomerization Versus Undesired Xylenes Loss Reactions Reactor temperature may be optimized to reduce catalyst load size (increase WHSV) while maintaining low/acceptable xylenes losses. FIGS. 1 and 2 show the weight of p-xylene to the total weight of all xylenes (p-xylene/xylenes ratio) as a function of WHSV and temperature and xylenes loss as a function of WHSV and temperature, respectively, in certain simulated LPI processes. FIG. 1 demonstrates in this case that the design WHSV can be doubled by increasing the operating temperature by approximately 20-30° C., while maintaining comparable p-xylene/xylenes ratio in the LPI product mixture effluent ("isomerization effluent"). As an example, a LPI reactor designed for a WHSV of 2.5 hour$^{-1}$ operating at 240° C. is estimated to achieve a p-xylene/xylenes ratio of 0.2347 in the isomerization effluent from a model feed composition. A LPI reactor designed for a WHSV of 5.0 hour$^{-1}$ (which requires only half the catalyst load in the reactor designed for WHSV of 2.5 hour$^{-1}$) operating at 260° C. is estimated to achieve a p-xylene/xylenes ratio of 0.2339 in the isomerization effluent. In a second example, a reactor designed for a WHSV or 10 hour$^{-1}$ operating at 290° C. is estimated to achieve p-xylene/xylenes ratio of 0.2355 in the isomerization effluent from a model feed composition. By raising the operating temperature by an additional 30° C. from 260° C., the reactor catalyst load size is again cut in half compared to a reactor designed for a WHSV of 5.0 hour$^{-1}$. These examples clearly demonstrate the ability to optimize design catalyst load size versus operating temperature to achieve similar p-xylene/xylenes ratio targets in the isomerization effluent.

Continuing with the examples provided in the above section, FIG. 2 demonstrates the trade off in xylenes losses as reactor temperature is optimized to reduce catalyst load size. In this disclosure, "xylenes loss" is calculated as the total concentration of all xylenes in the feed composition, expressed as the weight percentage of xylenes based on the total weight of the feed composition, minus the total concentration of xylenes in the product mixture effluent, expressed as the weight percentage of xylenes based on the total weight of the product mixture effluent. In the case of the first example (moving from WHSV at 2.5 hour$^{-1}$ at 240° C. to WHSV at 5 hour$^{-1}$ at 260° C.), the estimated impact in xylenes loss is an increase from 0.37% to 0.53% per pass. This per pass xylenes loss after the increases is still low, still comparable or better than in a typical vapor phase isomerization process. Therefore, the reduction in catalyst load size is advantageous for reducing capital investment at the expense of merely marginal debit in yields (i.e., marginal increase in xylenes loss). In the second example, the WHSV is further increased from 5 to 10 hour$^{-1}$ and the operating temperature is increased from 260 to 290° C. For this example the xylenes loss increases from 0.53% (at 5 hour$^{-1}$ WHSV and 260° C.) to 0.71% (at 10 hour$^{-1}$ and 290° C.). Again, the xylenes loss even after the increase is still low, comparable or better than in a typical vapor phase isomerization process. Therefore, the reduction in catalyst load size is advantageous for reducing capital investment at the expense of merely marginal debit in yields (i.e., marginal increase in xylenes loss).

The above examples demonstrate the ability to optimize load size and operating temperature to meet a target p-xylene/xylenes ratio in the isomerization effluent while reducing capital investment. One skilled in the art will recognize that optimizing in the reverse direction is also an option. One can opt for higher catalyst load and reduce xylenes loss reactions per pass by reducing temperature. However, as shown in FIG. 2, there will be a point of diminishing returns on xylenes loss reduction as temperature is further reduced. In Case 1 a single catalyst system is presumed in the simulation. While the temperature range and magnitude of effect may change with alternative catalyst systems (including multiple catalyst bed systems), the optimization method can be generally applied.

Case 2: Managing Catalyst Activity Loss/Aging with Temperature

Figure 3:
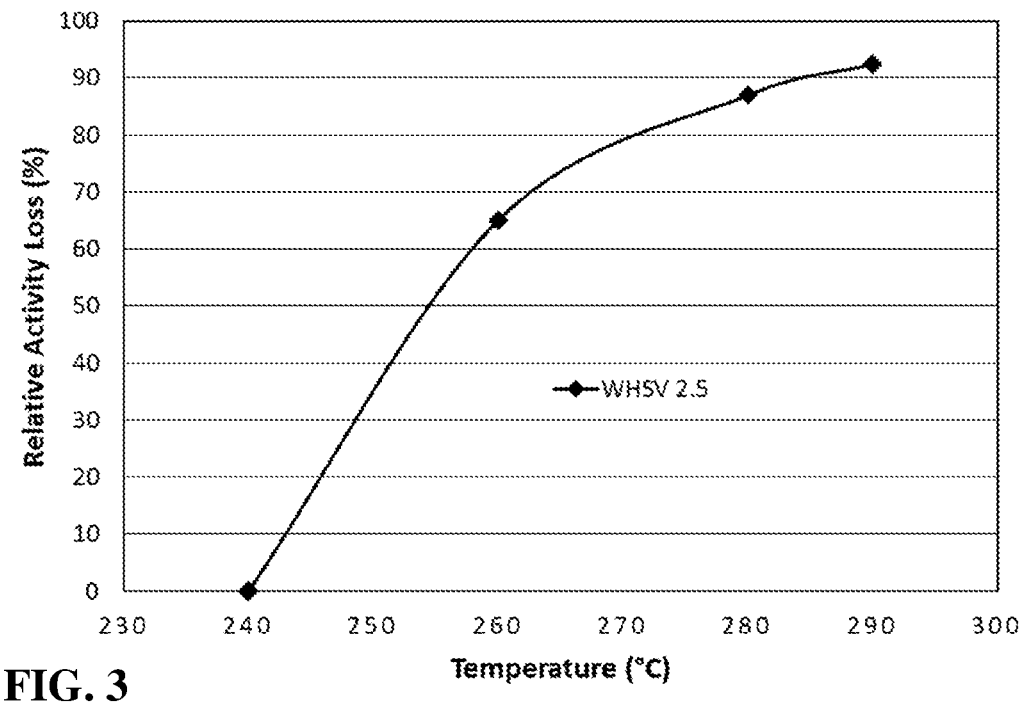
FIG. 3 is a graph showing relative activity loss of the isomerization catalyst as a function of reaction temperature at a WHSV of 2.5 hour-1 in a simulated LPI process of this disclosure.

Reactor temperature may also be used as a means of maintaining/optimizing reactor yields in response to catalyst activity loss (i.e., aging). FIG. 3 illustrates relative activity loss of the catalyst as a function of temperature in order to maintain a constant p-xylene/xylenes ratio in the product mixture effluent in a simulated LPI process operating at a WHSV of 2.5 hour$^{-1}$ for a particular isomerization feed composition. As can be seen from FIG. 3, as the catalyst activity declines (i.e., as the relative activity loss increases), the reaction temperature can be raised to maintain a constant p-xylene/xylenes ratio in the product mixture effluent. It should be recognized by one skilled in the art, that the relative xylenes losses will decline at various rates as well (at constant operating temperature, WHSV, Feed concentration) when catalyst activity loss occurs. The temperature increase to offset activity loss may be limited/set by optimizing between p-xylene/xylenes ratio in the product and xylenes loss per pass in the reactor.

Case 3: Determining Relative Activity Loss for a Given Reactor or Series of Reactors One can estimate the relative activity loss of a single catalyst system or multiple catalyst systems by monitoring various performance parameters as a function of temperature, feed rate, WHSV, and/or feed concentration which may include but are not limited to p-xylene/xylenes ratio in product, delta p-xylene/xylenes ratio across reactor, xylenes loss, toluene in product, benzene in product, trimethylbenzenes in product, methylethylbenzenes in product, total C9 aromatics ("A9") in product, total C10 aromatics ("A10") in product, total C9+ aromatics ("A9+") in the product, delta toluene across reactor, delta benzene across reactor, delta trimethylbenzenes across reactor, delta methylethylbenzenes across reactor, delta total A9 across reactor, delta total A10 across reactor, delta total A9+ across reactor, ethylbenzene conversion across reactor, non-aromatics conversion across the reactor (individual species, subset of species, or total non-aromatics), C5– products (individual species, subset of species, or total C5–), delta C5– across reactor (individual species, subset of species, or total C5–), or any combination of these parameters.

Figure 4:
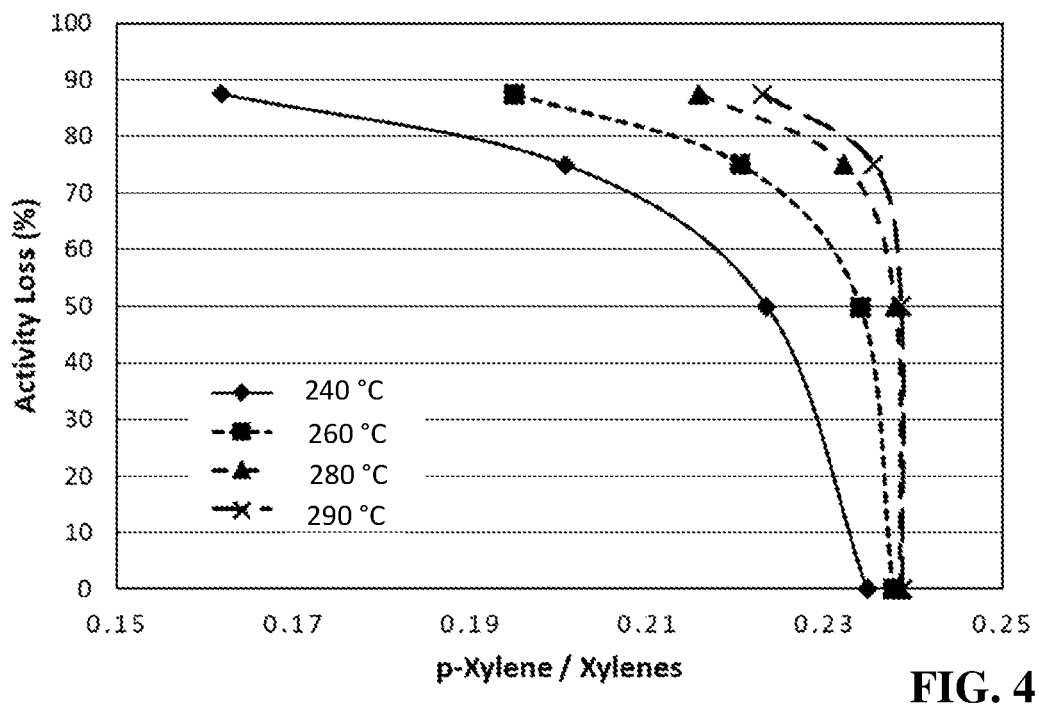
FIG. 4 is a graph showing activity loss of the isomerization catalyst as a function of p-xylene/xylenes at various temperatures in simulated LPI processes of this disclosure.

As an example, FIG. 4 illustrates using p-xylene/xylenes ratio in the product mixture effluent as an estimate relative activity loss. For this example, a constant 2.5 hour$^{-1}$ WHSV operation is assumed. In this example, temperature curves have been developed at 2.5 hour$^{-1}$ WHSV that correlate the p-xylene/xylenes ratio in the product to a relative activity loss. For illustrative purposes, let us assume that the catalyst system operating at 2.5 hour$^{-1}$ WHSV and 240° C. achieves p-xylene/xylenes ratio of 0.2234 in the product. This corresponds to ~50% relative activity loss from the fresh catalyst activity. In a second example, let us assume that the catalyst system operating at 2.5 hour$^{-1}$ WHSV and 280° C. achieves a p-xylene/xylenes ratio of 0.2321 in the product. This performance is indicative of approximately 75% relative activity loss from the fresh catalyst activity.

In the example of a lead-lag or multiple reactor system, the estimated relative activity loss or any of the parameters used in determining the estimated activity loss may be used to indicate/signal when to take a reactor/catalyst bed out of service. In the example provided in FIG. 4, the p-xylene/xylenes ratio curve demonstrates a sharp drop as activity loss extends past approximately 75%. Therefore, one plausible change-out strategy would be to use temperature increase to maintain yields until approximately 75% activity loss conditions are met, and then triggering taking the catalyst bed out of service once the 75% activity loss conditions are met/surpassed.

Case 4: Catalyst Activity De-Edging at Start of Run; Catalyst Activity Management During Operation Rate Turndown Opposite to Case 2, at start of cycle for a fresh catalyst bed it is common to have higher than desired initial catalyst activity that results in higher xylenes loss or undesirable levels of byproducts such as benzene, toluene, or A9+ molecules. This can also be the case at middle or end of run, if unit rates are substantially turned down below the design WHSV. To minimize the make of undesired byproducts at start of cycle or during significant turndown operation, the temperature can be lowered to reduce the undesired byproduct yield. In the case of "de-edging" initial fresh catalyst activity, the temperature can be gradually increased as the byproduct production rate declines over typically the first 1-2 months, but possibly up to 1 or more years for extreme cases. In the case, of unit rate turndown, the temperature can be adjusted as needed to manage yields. The absolute magnitude of temperature change will be dependent on percentage turndown from design rates as well as the relative activity loss that the catalyst has incurred on stream leading up to the turndown event.

Temperature control to manage higher than desired initial catalyst activity can also be used in multi-bed/multi reactor systems such as a lead-lag configurations. In the example of the lead-lag configuration, the fresh catalyst bed (whether lead or lag) can be started up at lower temperature versus the reactor that has already been on stream. The independent temperature control to the individual reactors can be managed by any number of configurations which may include but is not limited to; independent heaters/coolers on feed to each reactor, independent bypass lines around heaters/coolers to each reactor allowing for temperature control to each reactor, injection of a cooled or heated fresh stream to the lag reactor/reactors that is mixed with the effluent of the preceding reactor/reactors to control temperature to the lag reactor/reactors, utilizing natural heat loss between the lead-lag reactor/reactors to operate the lag reactor/reactors cooler than the lead reactor/reactors. Any combination of these temperature control methods may be used.

Case 5: Managing Lead Lag Configurations where the Reactor/Catalyst Bed Size Varies Between Lead and Lag As shown in Case 1, the reactor operating temperature can be manipulated to allow similar yields for reactors of varying catalyst load or WHSV. In a lead-lag or multi-reactor configuration, the reactors may be optimized/designed to have different quantities of catalyst. See TABLE II, for Cases 5a and 5b which are provided for illustration. In the TABLEs of this disclosure, for the purpose of brevity, EB means ethylbenzene, L-Paraffins means linear paraffins, BCNA means branched or cyclic non-aromatic hydrocarbons, MEBZ means methylethylbenzenes, DEBZ means diethylbenzenes, TriMBZ means trimethylbenzenes, and DMEBZ means dimethylethylbenzenes.

Case 5a estimates the yields for a lead-lag configuration where the lead catalyst bed operates at 5 hour$^{-1}$ WHSV and 240° C. and the lag catalyst bed operates at 10 hour$^{-1}$ WHSV and 260° C. In this Case, the bulk of the isomerization reaction occurs in the larger lead catalyst bed which allows for the use of a smaller lag bed operating at 10 hour$^{-1}$ WHSV and a slightly elevated temperature of 260° C. to serve as a finishing reactor for the xylene isomerization. Please note this combined lead-lag system with varied WHSV and temperature yields similar results to the larger single bed design case of 2.5 hour$^{-1}$ WHSV and 240° C. that is presented in the data in FIGS. 1 and 2 above.

Case 5b estimates the yields for a lead-lag configuration where the lead and lag catalyst beds operate at equivalent 10 hour$^{-1}$ WHSV each, but the operating temperatures are manipulated between the lead and lag reactors (240° C. for lead reactor, 270° C. for lag reactor). This configuration results in similar p-xylene/xylenes ratio in the product as Case 5a, but does have marginally higher estimated xylenes losses of 0.53% vs 0.46% xylenes loss for Case 5a.

the hydrogen co-feed may be reduced if the fresh catalyst activity to a given bed is undesirably high and resulting in high undesired byproduct make. Reducing the hydrogen co-feed during this "de-edging" period will help to promote/accelerate initial activity loss to reduce the period of high undesired byproduct make at start of cycle. As the undesired byproduct make declines, the hydrogen co-feed may be increased to reduce long term activity loss and to ultimately extend the run length of catalyst bed.

Hydrogen co-feed may be optimized through the cycle if increased rate of activity loss is observed at various operating conditions. For example, during periods where the observed rate of activity decline is high, the hydrogen co-feed may be increased. In periods where the observed rate of activity decline is low/negligible, the hydrogen co-feed may be decreased to reduce operating costs.

TABLE II

| | | Case 5a | | | | Case 5b | | | |
| | | \multicolumn{8}{c}{Stream Name} | | | | | | | |
| | | In-1 | Out-1 | In-2 | Out-2 | In-1 | Out-1 | In-2 | Out-2 |
|---|---|---|---|---|---|---|---|---|---|
| WHSV (Hour$^{-1}$) | | 5 | 5 | 10 | 10 | 10 | 10 | 10 | 10 |
| Temperature (° C.) | | 240 | 240 | 260 | 260 | 240 | 240 | 240 | 270 |
| Composition (wt %) | Benzene | 0.00 | 0.04 | 0.04 | 0.09 | 0.00 | 0.02 | 0.02 | 0.11 |
| | o-Xylene | 36.70 | 23.98 | 23.98 | 21.62 | 36.70 | 28.22 | 28.22 | 22.05 |
| | m-Xylene | 56.57 | 48.81 | 48.81 | 49.89 | 56.57 | 46.78 | 46.78 | 49.53 |
| | p-Xylene | 0.65 | 20.94 | 20.94 | 21.95 | 0.65 | 18.82 | 18.82 | 21.81 |
| | Toluene | 0.20 | 0.27 | 0.27 | 0.38 | 0.20 | 0.23 | 0.23 | 0.40 |
| | EB | 5.31 | 5.22 | 5.22 | 5.10 | 5.31 | 5.26 | 5.26 | 5.08 |
| | H$_2$ | 0.00 | 0.00 | 0.00 | 0.00 | 0.00 | 0.00 | 0.00 | 0.00 |
| | L-Paraffins | 0.49 | 0.49 | 0.49 | 0.49 | 0.49 | 0.49 | 0.49 | 0.49 |
| | BCNA | 0.05 | 0.05 | 0.05 | 0.05 | 0.05 | 0.05 | 0.05 | 0.05 |
| | MEBZ | 0.03 | 0.06 | 0.06 | 0.10 | 0.03 | 0.05 | 0.05 | 0.10 |
| | DEBZ | 0.01 | 0.02 | 0.02 | 0.03 | 0.01 | 0.01 | 0.01 | 0.04 |
| | TriMBZ | 0.00 | 0.06 | 0.06 | 0.17 | 0.00 | 0.03 | 0.03 | 0.20 |
| | DMEBZ | 0.00 | 0.05 | 0.05 | 0.13 | 0.00 | 0.03 | 0.03 | 0.15 |
| Xylenes Loss (wt %) | | | 0.18 | | 0.27 | | 0.09 | | 0.44 |
| p-Xylene/Xylenes ratio | | | 0.223 | | 0.235 | | 0.201 | | 0.234 |
| EB Conversion (%) | | | 1.68 | | 2.26 | | 0.85 | | 3.53 |
| Total Xylenes Loss (wt %) | | | | | 0.46 | | | | 0.53 |
| Total EB Conversion (%) | | | | | 3.94 | | | | 4.38 |

Case 6: Managing Hydrogen Co-Feed to Lead-Lag or Multi Reactor Systems

Low concentration hydrogen injection has been surprisingly found to attenuate/mitigate activity loss in liquid phase isomerization systems. It should be noted that the level of hydrogen co-feed to a lead-lag or multi reactor system can be controlled for only the inlet of the first reactor, or it can be separately controlled to each individual reactor or any subset of reactors/catalyst beds. The hydrogen level in the feed to each reactor may be controlled by any of the following means, but is not limited to the subset listed herein; independent hydrogen injection to any given reactor/reactors, addition of fresh feed to subsequent reactor/reactors that is combined with at least a portion of the effluent from the previous reactor/reactors, flashing of the effluent of a previous reactor/reactors to a lower pressure to remove hydrogen from the liquid phase prior to feeding at least a portion of the remaining liquid stream to the subsequent reactor/reactors.

Hydrogen co-feed may be optimized to individual reactors or any subset of reactors to minimize aging at varying WHSV, Temperature, or Feed Concentrations. It may also be manipulated/optimized over the cycle length of the catalyst in response to activity decline. For example, at start of cycle, Case 7: Optimizing WHSV, Temperature, Hydrogen Co-Feed for Single Bed or for Lead-Lag or Multi Reactor Systems Based on Feed Composition Feed concentration impacts both p-xylene/xylenes ratio in the isomerization effluent and the extent of undesired byproduct make. The concepts outlined in cases 1-6 above can also be applied to optimize yield and capital where significant feed compositional differences or variance is expected. Please see TABLE III for an illustration where a single bed reactor temperature is manipulated to achieve similar yields for a standard feed composition versus a high ortho-xylene containing feed. In this example, the standard feed contains low p-xylene (<1 wt %) content, low to moderate EB content (~5.3 wt %) and moderate o-xylene content (~37 wt %). The Ox-rich feed also contains low p-xylene (<1%), but also has low EB and m-xylene content (<1 wt % for both). In this example, when processing the Ox-rich feed, the single catalyst bed yields lower p-xylene/xylenes ratio in the product and lower xylenes loss when compared to processing standard feed at the same conditions of 2.5 hour$^{-1}$ WHSV and 240° C. However, in this example, the p-xylene/xylenes ratio in the product for the ortho-xylene rich feed case can be raised to match the standard feed product by raising the reactor temperature from 240° C.

to 250° C. As discussed in the above sections, optimization of WHSV, temperature, or a combination of both can be used to achieve equivalent product to the standard feed case.

TABLE III

|  |  | Standard Feed | | o-Xylene-Rich Feed | | | |
|---|---|---|---|---|---|---|---|
|  |  | Stream Name | | | | | |
|  |  | In-1 | Out-1 | In-1 | Out-1 | In-2 | Out-2 |
| WHSV |  | 2.5 | 2.5 | 2.5 | 2.5 | 2.5 | 2.5 |
| Temperature (° C.) |  | 240 | 240 | 240 | 240 | 250 | 250 |
| Composition | Benzene | 0.00 | 0.07 | 0.00 | 0.00 | 0.00 | 0.00 |
| (wt %) | o-Xylene | 36.70 | 21.36 | 98.50 | 24.39 | 98.50 | 22.79 |
|  | m-Xylene | 56.57 | 50.23 | 0.30 | 51.92 | 0.30 | 52.69 |
|  | p-Xylene | 0.65 | 21.95 | 0.10 | 22.41 | 0.10 | 23.08 |
|  | Toluene | 0.20 | 0.35 | 0.00 | 0.08 | 0.00 | 0.15 |
|  | EB | 5.31 | 5.13 | 0.10 | 0.10 | 0.10 | 0.10 |
|  | $H_2$ | 0.00 | 0.00 | 0.00 | 0.00 | 0.00 | 0.00 |
|  | L-Paraffins | 0.49 | 0.49 | 0.50 | 0.50 | 0.50 | 0.50 |
|  | BCNA | 0.05 | 0.05 | 0.00 | 0.00 | 0.00 | 0.00 |
|  | MEBZ | 0.03 | 0.10 | 0.50 | 0.50 | 0.50 | 0.50 |
|  | DEBZ | 0.01 | 0.03 | 0.00 | 0.00 | 0.00 | 0.00 |
|  | TriMBZ | 0.00 | 0.13 | 0.00 | 0.10 | 0.00 | 0.19 |
|  | DMEBZ | 0.00 | 0.10 | 0.00 | 0.00 | 0.00 | 0.00 |
| Xylenes Loss (wt %) |  |  | 0.37 |  | 0.18 |  | 0.35 |
| p-Xylene/xylenes ratio |  |  | 0.235 |  | 0.227 |  | 0.234 |
| EB Conversion (%) |  |  | 3.36 |  | 2.91 |  | 4.98 |

Figure 5:
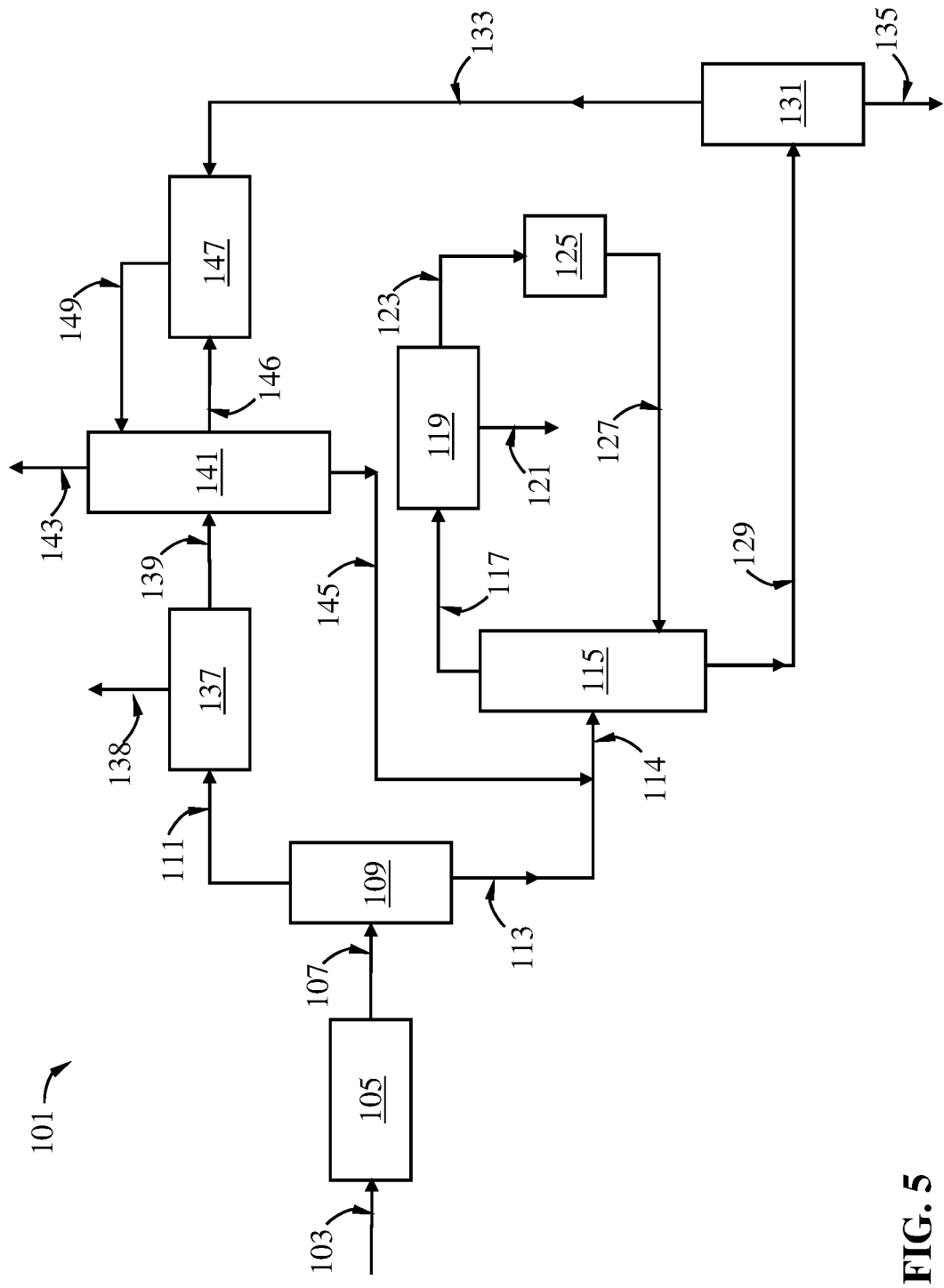
FIG. 5 is a schematic illustration of an aromatics production complex producing a p-xylene product from naphtha reforming.

FIG. 5: An Illustrative Aromatics Production Complex Producing a p-Xylene Product FIG. 5 schematically illustrates a process 101 for making xylenes, particularly a p-xylene product, from a reformate stream. In this figure, a heavy naphtha stream 103 produced from a crude oil refining process is supplied into a reforming zone 105. The reforming zone 105 can include one or more of any conventional naphtha catalytic reforming reactor(s), e.g., fixed-bed reactor(s), fluidized bed reactor(s), known in the art. A reforming catalyst is disposed in the reforming zone. On contacting the reforming catalyst under the reforming conditions such as those generally known in the art, hydrocarbons in the heavy naphtha stream 103 undergo a series of chemical reactions, including but not limited to isomerization, aromatization, dehydrocyclization, and the like, whereby at least a portion of the paraffins and naphthenes are converted into aromatic hydrocarbons. A reforming effluent 107 comprising C6+ aromatic hydrocarbons (including benzene, toluene, xylenes, ethylbenzene, and C9+ aromatic hydrocarbons) can be obtained from the reforming zone. The reforming effluent 107 or a portion thereof is then supplied into a reformate splitter 109 (e.g., a single distillation column, or a series of distillation columns), from which a C6-C7 hydrocarbons-rich stream 111 and a C8+ aromatic hydrocarbons-rich stream 113 are produced. The C6-C7 hydrocarbons-rich stream 111 comprises benzene, toluene, and their co-boiling paraffins and naphthenes, and the like. The C8+ aromatic hydrocarbons-rich stream 113 can comprise C8 aromatic hydrocarbons, and C9+ aromatic hydrocarbons. The C8+ aromatic hydrocarbons-rich stream 113, optionally in combination with other C8+ aromatics-rich stream(s) such as stream 145 (described below) as a joint stream 114, is then supplied to a xylenes splitter 115, from which a xylenes-rich stream 117 and a C9+ aromatic hydrocarbons-rich stream 129 are produced. The joint stream 114 is rich in C8+ aromatic hydrocarbons and lean in benzene, toluene, and co-boilers thereof compared to stream 107. The xylenes-rich stream 117 is rich in xylenes and ethylbenzene. The concentration of ethylbenzene in stream 117 can vary in a wide range. Stream 117 can comprise p-xylene at various concentrations, depending on the composition(s) of the C8+ aromatic hydrocarbons-rich stream(s) supplied to the xylenes splitter 115. For the purpose of producing a p-xylene product, the xylenes-rich stream 117 is typically supplied to a p-xylene recovery sub-system 119, from which a p-xylene product stream 121 rich in p-xylene and a p-xylene depleted stream 123 are produced. The p-xylene recovery sub-system 119 can be any crystallization-based and/or adsorption chromatography-based p-xylene separation systems known in the art. The p-xylene depleted stream 123, rich in m-xylene, o-xylene, and ethylbenzene compared to stream 117, is typically at least partly supplied to an isomerization zone 125 containing an isomerization catalyst disposed therein and operated under isomerization conditions. On contacting the isomerization catalyst under isomerization conditions, a portion of the m-xylene and o-xylene in stream 125 supplied into the isomerization zone 125 are converted into p-xylene. The isomerization effluent 127 exiting the isomerization zone 125 comprises p-xylene at a concentration higher than the p-xylene depleted stream 123. The isomerization effluent 127, or a portion thereof, is then supplied to the xylenes splitter 115. The xylenes splitter 115, the p-xylene recovery sub-system 119, and the isomerization zone 125 form a xylenes-loop.

The isomerization processes of this disclosure can be advantageously used in the process illustrated in FIG. 5.

As shown in FIG. 5, the C9+ aromatic hydrocarbons-rich stream 129 produced from the xylenes splitter 115, typically containing C9, C10, and C11+ aromatic hydrocarbons, is then separated in a distillation column 131 to obtain a C9-C10 aromatic hydrocarbons-rich stream 133 and a C11+ aromatic hydrocarbons-rich stream 135. Stream 135 is typically conducted away and used as, e.g., a motor gasoline blending stock, a fuel oil, and the like. Stream 133, along with a benzene/toluene-rich stream 146, is then supplied into a transalkylation zone 147 having a transalkylation catalyst disposed therein. In the presence of the transalkylation catalyst and under transalkylation conditions, the C9-C10 aromatic hydrocarbons react with benzene/toluene to produce xylenes. The C6-C7 hydrocarbons-rich stream 111 is typically supplied to an extraction distillation zone 137, where a C6-C7 aromatic hydrocarbons-rich stream 139 and an aromatic hydrocarbons-depleted raffinate stream 138 are produced. Stream 139 is then supplied to the benzene tower 141, from which a benzene product stream 143, a toluene-rich stream 146, and a C8+ aromatic hydrocarbons-rich stream 145 are produced. The toluene-rich stream 146, or a portion thereof, is supplied to the transalkylation 147 together with the C9-C10 aromatic hydrocarbons-rich stream 133 as described above. The C8+ aromatic hydrocarbons-rich stream 145 is then supplied to the xylenes splitter 115 along with stream 113, as described above.

This disclosure is further illustrated by the following non-limiting examples.

EXAMPLES

In the following examples, a C8 aromatic hydrocarbon feed stream consisting essentially of ethylbenzene, p-xylene, o-xylene and ethylbenzene was fed into a LPI reactor pre-loaded with a given quantity of a ZSM-5-based isomerization catalyst. A molecular hydrogen cylinder is connected to the LPI reactor or the C8 aromatic hydrocarbon feed stream source to enable co-feeding of it to the reactor at various feeding rates. The C8 aromatic hydrocarbon feed stream is heated to have a reactor inlet temperature in the range from 200 to 300° C. The pressure in the reactor was in the range from 689 to 3447 kPa (gauge). Under such conditions, C8 aromatic hydrocarbon present in the reactor was substantially entirely in liquid phase, and molecular hydrogen co-fed into the reactor, if any, was substantially entirely dissolved in the liquid phase of the hydrocarbons. The isomerization conditions were varied to test the deactivation of the isomerization catalyst. The isomerization effluent exiting the isomerization reactor was then analyzed by using gas chromatography to determine the concentrations (wt %) of p-xylene, o-xylene, and m-xylene, based on the total weight of the isomerization effluent. The measured p-xylene concentration (C(pX), wt %), o-xylene concentration (C(oX), wt %), and m-xylene concentration (C(mX), wt %) were then used to calculate the p-xylene concentration based on the total quantity of xylenes (C(pX/X), %) according to the following formula:

$$C(pX/X) = \frac{C(pX)}{C(pX) + C(oX) + C(mX)} \times 100\%$$

In the description of these examples, "CGpGC" means cumulative weight of the C8 aromatic hydrocarbon feed in grams per gram of the isomerization catalyst that has been processed by the batch of the isomerization catalyst. In a hypothetical case where the feeding rate of the C8 aromatic hydrocarbon feed is maintained constant, CGpGC would correspond to the product of the feeding rate and time on stream of the catalyst.

Example 1

Figure 6:
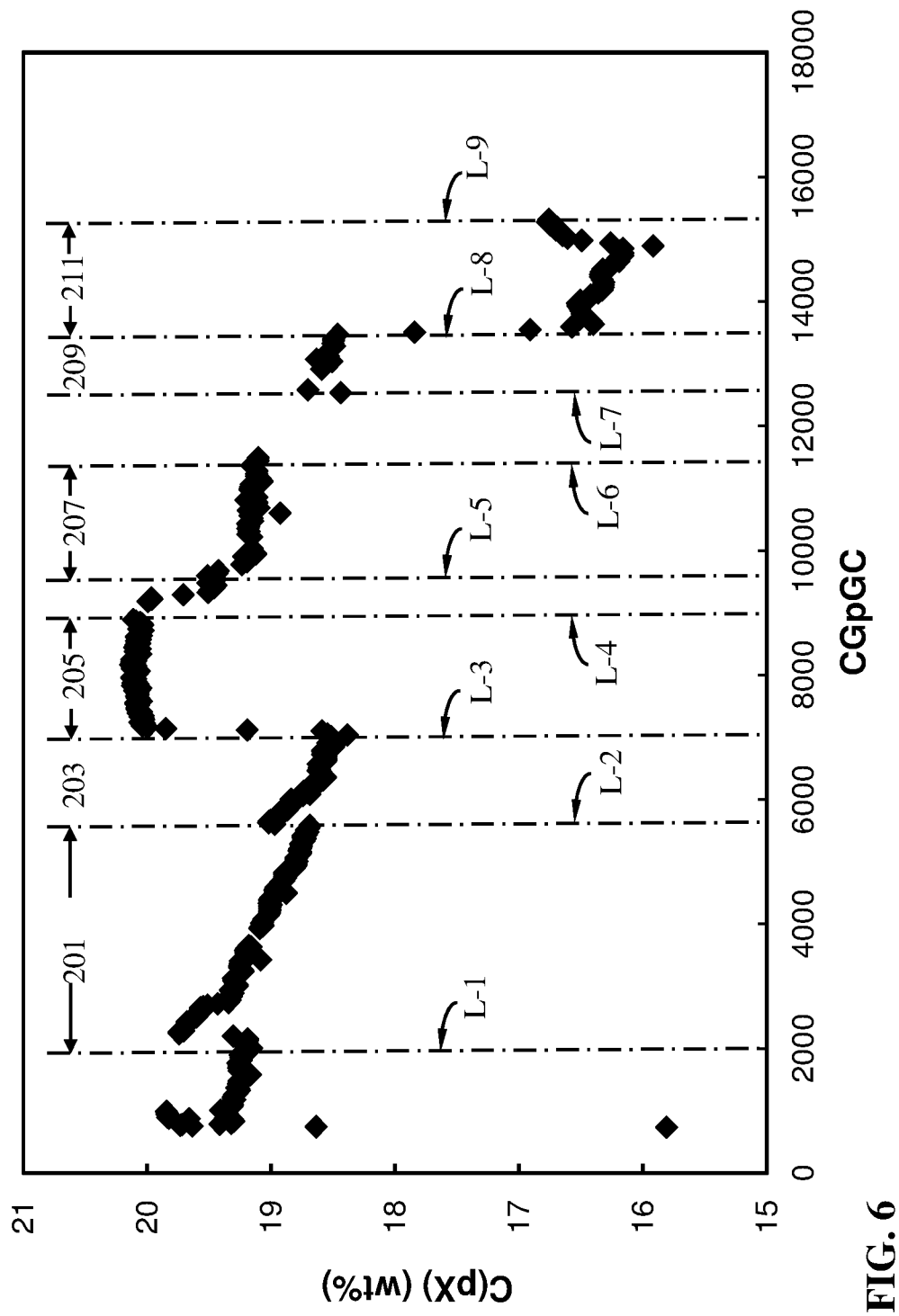
FIG. 6 is graph showing p-xylene concentration in the isomerization effluent as a function of cumulative grams of feed per gram of the isomerization catalyst ("CGpGC") of a LPI process operated under various isomerization conditions, demonstrating various catalyst deactivation rates, particularly under various feeding rates of molecular hydrogen and various WHSV.

In this example, the C8 aromatic hydrocarbon feed stream comprised 3.4 wt % of p-xylene, 64.1 wt % of m-xylene, 18.3 wt % of o-xylene, 12.3 wt % of ethylbenzene, and 1.3 wt % of other hydrocarbons. In the isomerization process, isomerization conditions such as WHSV and feeding rate of molecular hydrogen were varied. The reactor pressure was varied in order to maintain the molecular hydrogen co-fed at various feeding rate into the isomerization reactor substantially entirely dissolved in the liquid phase C8 aromatic hydrocarbons. The reaction temperature in the isomerization reactor was maintained at approximately 280° C. p-Xylene concentration in the isomerization effluent as a function of CGpGC in the process is shown in FIG. 6. WHSV (hour$^{-1}$) and feeding rate of molecular hydrogen (C(H$_2$), ppm by weight of molecular hydrogen based on the weight of the C8 aromatic hydrocarbon feed stream) during various CGpGC ranges shown in FIG. 6 are provided in TABLE II below. In FIG. 6, CGpGC range 201 is defined by the two vertical lines L-1 and L-2, range 203 by vertical lines L-2 and L-3, range 205 by vertical lines L-3 and L-4, range 207 by vertical lines L-5 and L-6, range 209 by vertical lines L-7 and L-8, and range 211 by vertical lines L-8 and L-9.

TABLE II

|  | CGpGC Range | | | | | |
| --- | --- | --- | --- | --- | --- | --- |
|  | 201 | 203 | 205 | 207 | 209 | 211 |
| WHSV (hour$^{-1}$) | 10 | 10 | 10 | 20 | 20 | 20 |
| H$_2$ Co-feeding Rate (ppm) | 7 | 0 | 255 | 255 | 0 | 0 |

As can be seen in FIG. 6, in CGpGC range 201, at a WHSV of 10 hour$^{-1}$ and a molecular hydrogen feeding rate of 7 ppm, the concentration of p-xylene in the isomerization effluent (C(pX), wt %) declined steadily, indicating that the activity of the catalyst decreased steadily. Throughout range 203, at a WHSV of 10 hour$^{-1}$ and in the absence of co-feeding molecular hydrogen into the isomerization reactor, the C(pX) continued its decline similar to in range 201, indicating similar deactivation rate of the isomerization catalyst in the absence of co-fed molecular hydrogen. The data in ranges 201 and 203 demonstrate that at a high WHSV of 10 hour$^{-1}$, the isomerization catalyst deactivated relatively fast when no molecular hydrogen was co-fed, and when molecular hydrogen was co-fed at a low rate of 7 ppm.

At the end of CGpGC range 203 and the beginning of range 205, the molecular hydrogen feeding rate was increased to 255 ppm while the WHSV was maintained at 10 hour$^{-1}$, which were then maintained throughout range 205. At the beginning of range 205, the C(pX) increased substantially compared to at any CGpGC in ranges 203 and 201, indicating a substantial increase of the activity of the isomerization catalyst in the presence of a substantially increased molecular hydrogen concentration in the reactor. Throughout range 205, the C(pX) was substantially steady, indicating little deactivation of the isomerization catalyst in the presence of molecular hydrogen at 255 ppm at a high WHSV of 10 hour$^{-1}$.

At the end of CGpGC range 205, the WHSV was ramped up while the feeding rate of molecular hydrogen was maintained at 255 ppm. During range 207, the WHSV and the feeding rate of molecular hydrogen were maintained at 20 hour$^{-1}$ and 255 ppm, respectively. The C(pX) in range 207 was lower compared to in range 205, which is understandable due to the twice as high of WHSV in range 207. Nonetheless, the C(pX) throughout range 207 was significantly higher than at the ends of ranges 201 and 203, even though the WHSV in range 207 is twice as high as in ranges 201 and 203, clearly demonstrating a significantly higher activity of the isomerization catalyst in range 207 than in ranges 201 and 203, and the effect of a high molecular hydrogen concentration in the isomerization reactor on the activity of the catalyst. Moreover, during range 207, once the C(pX) stabilized, it decreased very little, showing a very low deactivation rate of the isomerization catalyst even at a very high WHSV of 20 hour$^{-1}$, indicating the substantial effect imparted by the high concentration of molecular hydrogen in the isomerization reactor.

At the end of range 207, the feeding rate of molecular hydrogen was reduced. During range 209, no molecular hydrogen was fed into the reactor, and the WHSV was maintained a 20 hour$^{-1}$. As a result of the absence of molecular hydrogen in the isomerization reactor, the C(pX) decreased substantially in range 209 compared to in range 207, again demonstrating the effect of the presence of molecular hydrogen in the isomerization reactor on the activity of the isomerization catalyst. The C(pX) in range 209 was similar to at the end of range 203 where no molecular hydrogen was fed into the reactor as well.

At the end of range 209, a catalyst deactivating agent was injected into the reactor to expedite the deactivation of the isomerization catalyst. Afterwards, during range 211, the WHSV was maintained at 20 hour$^{-1}$ while no molecular hydrogen was co-fed into the reactor. C(pX) in range 211 was low as a result of the deactivated catalyst, a high WHSV of 20 hour$^{-1}$, and the absence of molecular hydrogen co-fed into the reactor.

This Example 1 clearly demonstrates that in a liquid-phase LPI process, by co-feeding molecular hydrogen at a feeding rate of ≥100 ppm, based on the total weight of the C8 aromatic hydrocarbon isomerization feed, the activity of the isomerization catalyst was enhanced, and the deactivation of the catalyst was reduced substantially, compared to feeding molecular hydrogen at a low feeding rate or no co-feeding of molecular hydrogen. Given the high activity and exceedingly low deactivation rate of the isomerization catalyst shown at high molecular hydrogen concentration, a LPI process at very high WHSV of, e.g., ≥10 hour$^{-1}$, ≥15 hour$^{-1}$, ≥17.5 hour$^{-1}$, and even ≥20 hour$^{-1}$, can be enabled by co-feeding molecular hydrogen into the isomerization reactor at ≥100 ppm.

Example 2 (Comparative)

Figure 7:
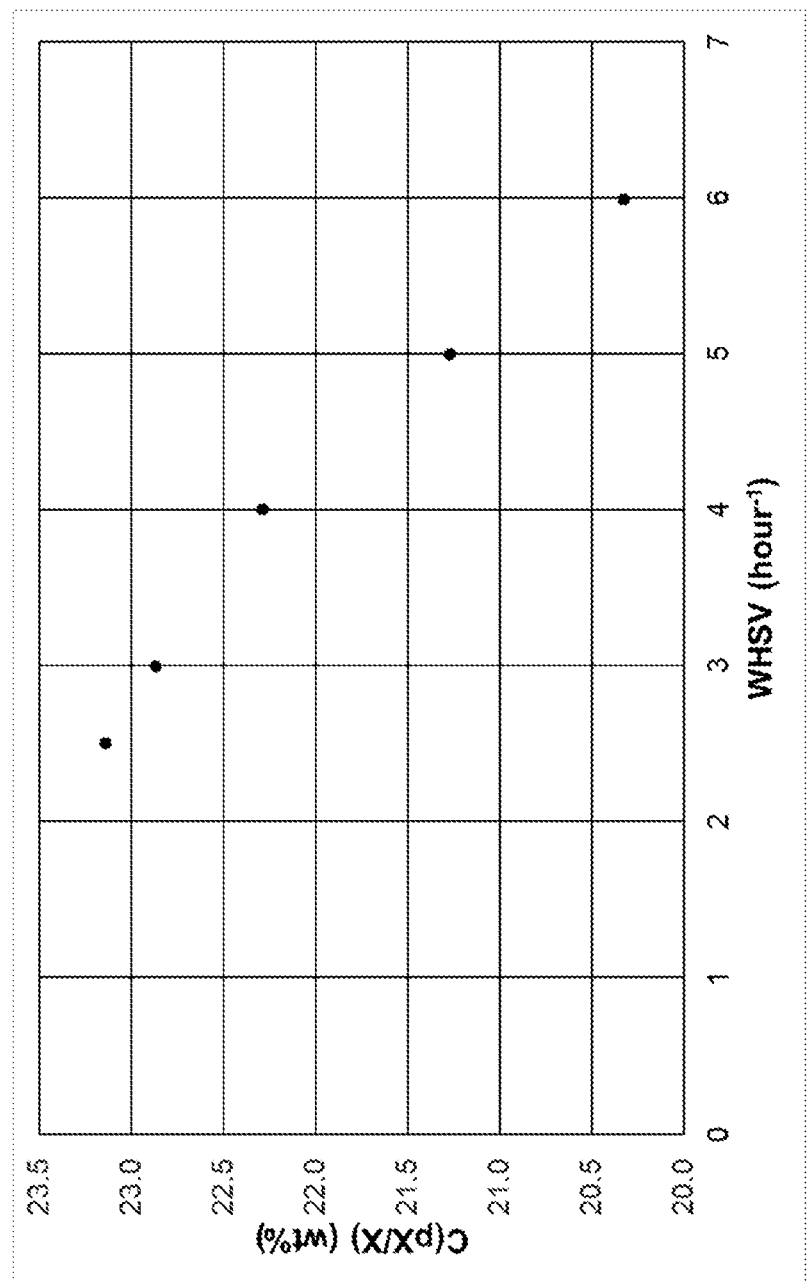
FIG. 7 is graph showing p-xylene concentration in the isomerization effluent of a comparative LPI process as a function of WHSV, operated under isomerization conditions including sparging molecular hydrogen at 9 ppm into the isomerization hydrocarbon feed and feeding a C8 aromatic hydrocarbon feed comprising ethylbenzene at a low concentration of approximately 1 wt %, demonstrating fast catalyst deactivation in the presence of a low molecular hydrogen concentration in the isomerization hydrocarbon feed.

In this example, the C8 aromatic hydrocarbon feed stream comprised 1.1 wt % of p-xylene, 67.7 wt % of m-xylene, 29.8 wt % of o-xylene, 1 wt % of ethylbenzene, and 0.5 wt % of other hydrocarbons. In the isomerization process, the WHSV was varied, the feeding rate of molecular hydrogen was maintained at 9 ppm by weight, based on the weight of the C8 aromatic hydrocarbon feed stream. The reaction temperature in the isomerization reactor was maintained at approximately 239° C. The reactor pressure was sufficient to maintain the molecular hydrogen co-fed into the isomerization reactor substantially entirely dissolved in the liquid phase C8 aromatic hydrocarbons. p-Xylene concentration in the isomerization effluent based on the total quantity of xylenes (C(pX/X), wt %) as a function of WHSV (hour$^{-1}$) in the process is shown in FIG. 7.

The feed stream used in this example is deemed as relatively easy to isomerize due to the low concentration of ethylbenzene therein. Thus, one would appreciate similar performance of the catalyst at high WHSV. Nonetheless, as FIG. 7 clearly shows, as the WHSV increased from 2.5 to 6 hour$^{-1}$, C(pX/X) decreased significantly, indicating that the catalyst deactivated when the WHSV increased, even at a relatively low WHSV range from 2.5 to 6 hour$^{-1}$. This example shows that co-feeding molecular hydrogen at a low feeding rate of 9 ppm does not provide appreciable benefit to the deactivation of the isomerization catalyst even if a benign feed comprising ethylbenzene at a low concentration is used.

Example 3 (Comparative)

Figure 8:
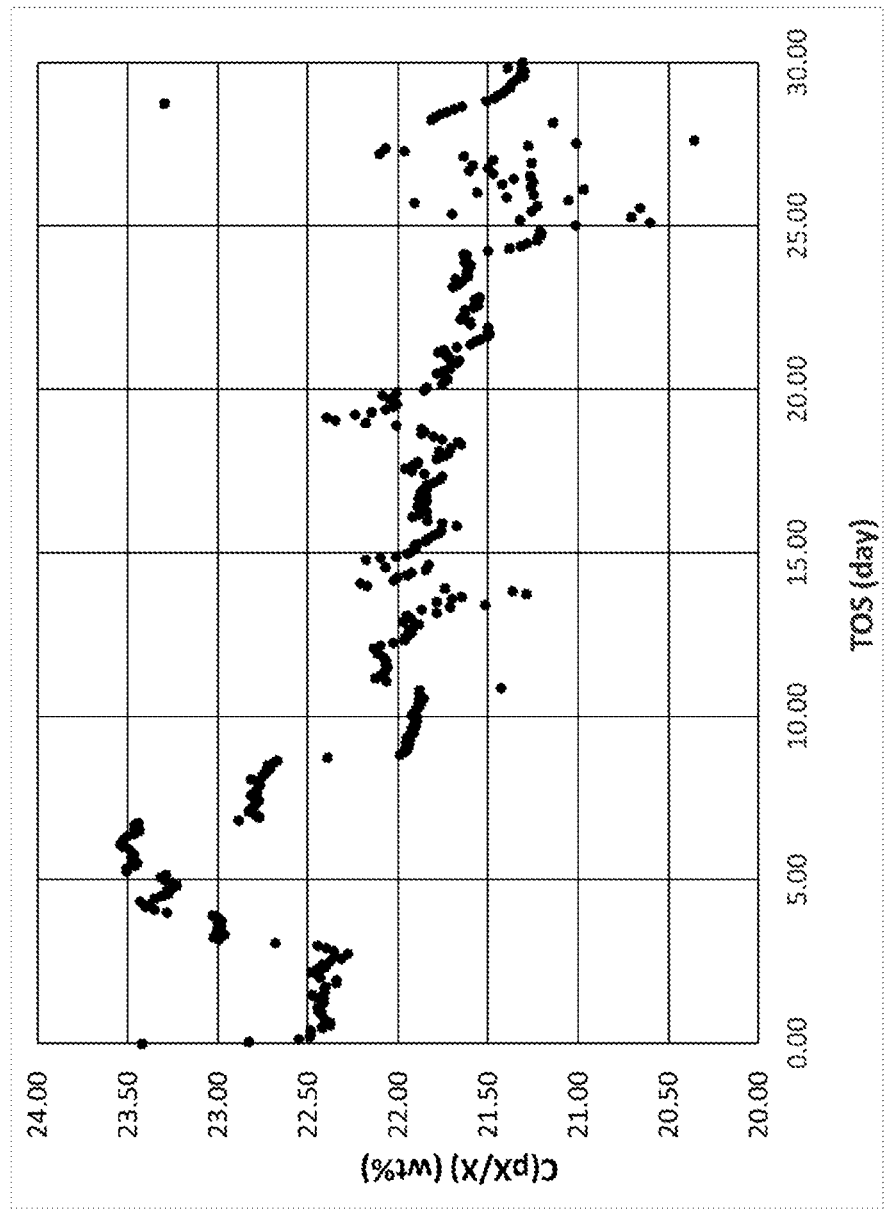
FIG. 8 is a graph showing p-xylene concentration (wt %) in the isomerization effluent of another comparative LPI process as a function of time on stream, operated under a WHSV of 4 hour$^{-1}$ but without co-feeding into the LPI reactor, wherein the isomerization hydrocarbon feed comprised p-xylene at a high concentration of 9 wt %, demonstrating a fast catalyst deactivation in the absence of co-fed molecular hydrogen even if the isomerization hydrocarbon feed is presumed to be less likely to cause catalyst deactivation.

In this example, the C8 aromatic hydrocarbon feed stream comprised 8.1 wt % of p-xylene, 58.1 wt % of m-xylene, 24.4 wt % of o-xylene, 7.5 wt % of ethylbenzene, and 1.9 wt % of other hydrocarbons. In the isomerization process, the WHSV was maintained at 4 hour$^{-1}$. No molecular hydrogen was fed into the isomerization reactor. The reaction temperature in the isomerization reactor was maintained at approximately 239° C. p-Xylene concentration in the isomerization effluent based on the total quantity of xylenes (C(pX/X), wt %) as a function of Time on Stream (TOS, day) in the process is shown in FIG. 8.

The feed stream used in this example is deemed as relatively easy to isomerize due to the high concentration of p-xylene therein. Thus, one would expect a high performance of the catalyst at a WHSV of 4 hour$^{-1}$. Nonetheless, as FIG. 8 clearly shows, C(pX/X) decreased significantly over a period of only 25 days, indicating that the catalyst activity deactivated appreciably in a relatively short period of time at a relatively low WHSV of 4 hour$^{-1}$.

With this example taken into consideration, the positive effect of co-feeding molecular hydrogen at a high feeding rate of ≥100 ppm in Example 1 in reducing deactivation of the isomerization catalyst is further demonstrated.

What is claimed is:

1. A process comprising:
   co-feeding molecular hydrogen and a liquid phase isomerization hydrocarbon feed comprising C8 aromatic hydrocarbons into an isomerization reactor having a ZSM-5 isomerization catalyst disposed therein, wherein the co-feeding comprises feeding the molecular hydrogen at a feeding rate from 200 ppm to less than or equal to 1000 ppm by weight, based on the total weight of the isomerization hydrocarbon feed; and
   contacting the molecular hydrogen and the C8 aromatic hydrocarbons with the ZSM-5 isomerization catalyst under isomerization conditions in the isomerization reactor to produce an isomerization effluent, wherein the isomerization conditions comprise a reaction pressure in the isomerization reactor from 1,700 kPa-gauge to 3,500 kPa-gauge and a reaction temperature such that the C8 aromatic hydrocarbons are substantially in a liquid phase in the isomerization reactor, and a weight hourly space velocity from 5 to 20 hour$^{-1}$.

2. The process of claim 1, wherein the C8 aromatic hydrocarbons are substantially entirety in the liquid phase in the isomerization reactor.

3. The process of claim 1, wherein at least a portion of the molecular hydrogen is dissolved in the liquid phase of the isomerization hydrocarbon feed before being fed into the isomerization reactor.

4. The process of claim 1, wherein the isomerization conditions comprise the reaction temperature in the isomerization reactor of from 200 to 300° C.

5. The process of claim 4, wherein the isomerization conditions comprise the reaction temperature in the isomerization reactor of from 240 to 300° C.

6. The process of claim 5, wherein the isomerization conditions comprise the reaction temperature in the isomerization reactor of from 260 to 300° C., and the weight hourly space velocity of from 10 to 20 hour$^{-1}$.

7. The process of claim 1, wherein the isomerization hydrocarbon feed comprises ethylbenzene at a concentration no greater than 20 wt %, based on the total weight of the isomerization hydrocarbon feed.

8. The process of claim 1, wherein the isomerization hydrocarbon feed comprises p-xylene at a concentration no greater than 10 wt %.

9. The process of claim 1, wherein the ZSM-5 isomerization catalyst is free of precious metals and comprises a silica to alumina molar ratio ranging from about 20 to about 50.

10. The process of claim 1, wherein the ZSM-5 isomerization catalyst comprises a first metal element selected from Fe, Co, Ni, Ru, Rh, Pd, Re, Os, Ir, Pt, and combinations thereof, and optionally a second metal element selected from Sn, Zn, Ag, and combinations thereof.

11. The process of claim 1, further comprising:
increasing the reaction temperature and/or the weight hourly space velocity without decreasing the p-xylene/xylenes weight ratio in the isomerization effluent by greater than or equal to 10%.

12. The process of claim 1, further comprising:
increasing the reaction temperature by 20 to 30° C. and/or the weight hourly space velocity without substantially increasing xylenes loss by greater than or equal to 10%.

13. The process of claim 1, further comprising increasing the feeding rate of the molecular hydrogen after the beginning phase of a catalyst cycle.

14. The process of claim 1, further comprising:
increasing the reaction temperature and/or the weight hourly space velocity without decreasing the p-xylene/xylenes weight ratio in the isomerization effluent by greater than or equal to 10%.

15. The process of claim 1, further comprising increasing the feeding rate of the molecular hydrogen after the beginning phase of a catalyst cycle.

16. The process of claim 1, wherein the isomerization conditions the weight hourly space velocity from 7.5 to 20 hour$^{-1}$.

17. The process of claim 1, wherein the isomerization conditions the weight hourly space velocity from 10 to 20 hour$^{-1}$.

18. The process of claim 1, wherein the molecular hydrogen is fed into the isomerization reactor at the feeding rate of from 200 ppm to 500 ppm by weight, based on the total weight of the isomerization hydrocarbon feed.

19. The process of claim 1, wherein the co-feeding comprises feeding the molecular hydrogen at a feeding rate of about 255 ppm.

20. A process for producing p-xylene, the process comprising:
co-feeding molecular hydrogen and a liquid phase isomerization hydrocarbon feed comprising C8 aromatic hydrocarbons into an isomerization reactor having a ZSM-5 isomerization catalyst disposed therein, wherein the co-feeding comprises feeding the molecular hydrogen at a feeding rate from 200 ppm to less than or equal to 1000 ppm by weight, based on the total weight of the isomerization hydrocarbon feed; and
contacting the molecular hydrogen and the C8 aromatic hydrocarbons with the ZSM-5 isomerization catalyst under isomerization conditions in the isomerization reactor to produce an isomerization effluent, wherein the isomerization conditions comprise a reaction pressure from 1,700 kPa-gauge to 3,500 kPa-gauge and a reaction temperature of from 200 to 300° C. such that the C8 aromatic hydrocarbons are substantially in a liquid phase in the isomerization reactor, and a weight hourly space velocity from 5 to 20 hour$^{-1}$; the isomerization effluent comprises p-xylene at a concentration higher than the isomerization hydrocarbon feed; and
recovering at least a portion of the p-xylene from the isomerization effluent.

21. The process of claim 20, wherein the molecular hydrogen is fed into the isomerization reactor at the feeding rate of 200 ppm to 500 ppm by weight, based on the total weight of the isomerization hydrocarbon feed.

22. The process of claim 20, wherein the C8 aromatic hydrocarbons are substantially entirety in the liquid phase in the isomerization reactor.

23. The process of claim 22, wherein at least 98% of the C8 aromatic hydrocarbons are in the liquid phase in the isomerization reactor.

24. The process of claim 22, wherein at least 98% of the molecular hydrogen is dissolved in the liquid phase of the C8 aromatic hydrocarbons in the isomerization reactor.

25. The process of claim 20, wherein the ZSM-5 isomerization catalyst comprises a first metal element selected from Fe, Co, Ni, Ru, Rh, Pd, Re, Os, Ir, Pt, and combinations thereof, and optionally a second metal element selected from Sn, Zn, Ag, and combinations thereof.

* * * * *